US005876969A

United States Patent [19]

Fleer et al.

[11] Patent Number: 5,876,969

[45] Date of Patent: Mar. 2, 1999

[54] FUSION POLYPEPTIDES COMPRISING HUMAN SERUM ALBUMIN, NUCLEIC ACIDS ENCODING SAME, AND RECOMBINANT EXPRESSION THEREOF

[76] Inventors: Reinhard Fleer, 47, av Beauséjour, 91440 Bures-sur-Yvette, France; Alain Fournier, 28, av Roger Salengro, 92000 Châtenay-Malabry, France; Jean-Dominique Guitton, 74, rue Dunois, 75013 Paris, France; Gérard Jung, 12, rue des Grands Jardins, Leuville-sur-Orge, 91310 Montlhery, France; Patrice Yeh, 11 bis, rue lacepède, 75005 Paris, France

[21] Appl. No.: 797,689

[22] Filed: Jan. 31, 1997

Related U.S. Application Data

[63] Continuation of Ser. No. 256,927, filed as PCT/FR93/00085, Jan. 28, 1993, abandoned.

[30] Foreign Application Priority Data

Jan. 31, 1992 [FR] France .................................. 92-01064

[51] Int. Cl.[6] .......................... C07K 14/00; C12N 1/19; C12N 1/21; C12N 5/10

[52] U.S. Cl. .................... 435/69.7; 435/320.1; 435/325; 435/252.3; 536/23.4; 536/24.1; 530/350; 530/362; 514/12

[58] Field of Search ......................... 536/23.4; 435/24.1, 435/69.7, 320.1, 325, 252.3; 530/350, 362; 514/12

[56] References Cited

FOREIGN PATENT DOCUMENTS

| | | |
|---|---|---|
| 413622 | 8/1990 | European Pat. Off. . |
| 3201987 | 12/1989 | Japan . |
| WO89/02922 | 10/1988 | WIPO . |
| WO90/13653 | 4/1990 | WIPO . |
| WO93/00437 | 6/1992 | WIPO . |

OTHER PUBLICATIONS

Uhlen, M. et al., *Methods in Enzymology,* 185 :129–143, 1990.

*Primary Examiner*—Elizabeth Kemmerer
*Attorney, Agent, or Firm*—Synnestvedt & Lechner

[57] ABSTRACT

Biologically active polypeptides comprising a therapeutically active polypeptide fused to human serum albumin or a natural variant thereof, methods for the preparation thereof, nucleotide sequences encoding such fusion polypeptides, expression cassettes comprising such nucleotide sequences, self-replicating plasmids containing such expression cassettes, and pharmaceutical compositions containing said fusion polypeptides.

15 Claims, 25 Drawing Sheets

NH2
COOH
M/LP
PEP
HSA
PEP
Peptide linker (optional)
Peptide linker (optional)

```
AAGCT TTACAACAAA TATAAAAACA ATG AAG TGG GTA ACC TTT ATT TCC CTT CTT TTT CTC TTT
                            Met Lys Trp Val Thr Phe Ile Ser Leu Leu Phe Leu Phe  -12

AGC TCG GCT TAT TCC AGG GGT GTG TTT CGT CGA GAT GCA CAC AAG AGT GAG GTT GCT CAT
Ser Ser Ala Tyr Ser Arg Gly Val Phe Arg Arg Asp Ala His Lys Ser Glu Val Ala His    9

CGG TTT AAA GAT TTG GGA GAA GAA AAT TTC AAA GCC TTG GTG TTG ATT GCC TTT GCT CAG
Arg Phe Lys Asp Leu Gly Glu Glu Asn Phe Lys Ala Leu Val Leu Ile Ala Phe Ala Gln   29

TAT CTT CAG CAG TGT CCA TTT GAA GAT CAT GTA AAA TTA GTG AAT GAA GTA ACT GAA TTT
Tyr Leu Gln Gln Cys Pro Phe Glu Asp His Val Lys Leu Val Asn Glu Val Thr Glu Phe   49

GCA AAA ACA TGT GTT GCT GAT GAG TCA GCT GAA AAT TGT GAC AAA TCA CTT CAT ACC CTT
Ala Lys Thr Cys Val Ala Asp Glu Ser Ala Glu Asn Cys Asp Lys Ser Leu His Thr Leu   69

TTT GGA GAC AAA TTA TGC ACA GTT GCA ACT CTT CGT GAA ACC TAT GGT GAA ATG GCT GAC
Phe Gly Asp Lys Leu Cys Thr Val Ala Thr Leu Arg Glu Thr Tyr Gly Glu Met Ala Asp   89

TGC TGT GCA AAA CAA GAA CCT GAG AGA AAT GAA TGC TTC TTG CAA CAC AAA GAT GAC AAC
Cys Cys Ala Lys Gln Glu Pro Glu Arg Asn Glu Cys Phe Leu Gln His Lys Asp Asp Asn  109

CCA AAC CTC CCC CGA TTG GTG AGA CCA GAG GTT GAT GTG ATG TGC ACT GCT TTT CAT GAC
Pro Asn Leu Pro Arg Leu Val Arg Pro Glu Val Asp Val Met Cys Thr Ala Phe His Asp  129

AAT GAA GAG ACA TTT TTG AAA AAA TAC TTA TAT GAA ATT GCC AGA AGA CAT CCT TAC TTT
Asn Glu Glu Thr Phe Leu Lys Lys Tyr Leu Tyr Glu Ile Ala Arg Arg His Pro Tyr Phe  149

TAT GCC CCG GAA CTC CTT TTC TTT GCT AAA AGG TAT AAA GCT GCT TTT ACA GAA TGT TGC
Tyr Ala Pro Glu Leu Leu Phe Phe Ala Lys Arg Tyr Lys Ala Ala Phe Thr Glu Cys Cys  169

CAA GCT GCT GAT AAA GCT GCC TGC CTG TTG CCA AAG CTC GAT GAA CTT CGG GAT GAA GGG
Gln Ala Ala Asp Lys Ala Ala Cys Leu Leu Pro Lys Leu Asp Glu Leu Arg Asp Glu Gly  189
```

FIG. 2A

```
AAG GCT TCG TCT GCC AAA CAG AGA CTC AAG TGT GCC AGT CTC CAA AAA TTT GGA GAA AGA
Lys Ala Ser Ser Ala Lys Gln Arg Leu Lys Cys Ala Ser Leu Gln Lys Phe Gly Glu Arg  209

GCT TTC AAA GCA TGG GCA GTA GCT CGC CTG AGC CAG AGA TTT CCC AAA GCT GAG TTT GCA
Ala Phe Lys Ala Trp Ala Val Ala Arg Leu Ser Gln Arg Phe Pro Lys Ala Glu Phe Ala  229

GAA GTT TCC AAG TTA GTG ACA GAT CTT ACC AAA GTC CAC ACG GAA TGC TGC CAT GGA GAT
Glu Val Ser Lys Leu Val Thr Asp Leu Thr Lys Val His Thr Glu Cys Cys His Gly Asp  249

CTG CTT GAA TGT GCT GAT GAC AGG GCG GAC CTT GCC AAG TAT ATC TGT GAA AAT CAA GAT
Leu Leu Glu Cys Ala Asp Asp Arg Ala Asp Leu Ala Lys Tyr Ile Cys Glu Asn Gln Asp  269

TCG ATC TCC AGT AAA CTG AAG GAA TGC TGT GAA AAA CCT CTG TTG GAA AAA TCC CAC TGC
Ser Ile Ser Ser Lys Leu Lys Glu Cys Cys Glu Lys Pro Leu Leu Glu Lys Ser His Cys  289

ATT GCC GAA GTG GAA AAT GAT GAG ATG CCT GCT GAC TTG CCT TCA TTA GCT GCT GAT TTT
Ile Ala Glu Val Glu Asn Asp Glu Met Pro Ala Asp Leu Pro Ser Leu Ala Ala Asp Phe  309

GTT GAA AGT AAG GAT GTT TGC AAA AAC TAT GCT GAG GCA AAG GAT GTC TTC CTG GGC ATG
Val Glu Ser Lys Asp Val Cys Lys Asn Tyr Ala Glu Ala Lys Asp Val Phe Leu Gly Met  329

TTT TTG TAT GAA TAT GCA AGA AGG CAT CCT GAT TAC TCT GTC GTA CTG CTG CTG AGA CTT
Phe Leu Tyr Glu Tyr Ala Arg Arg His Pro Asp Tyr Ser Val Val Leu Leu Leu Arg Leu  349

GCC AAG ACA TAT GAA ACC ACT CTA GAG AAG TGC TGT GCC GCT GCA GAT CCT CAT GAA TGC
Ala Lys Thr Tyr Glu Thr Thr Leu Glu Lys Cys Cys Ala Ala Ala Asp Pro His Glu Cys  369

TAT GCC AAA GTG TTC GAT GAA TTT AAA CCT CTT CTT GAA GAG CCT CAG AAT TTA ATC AAA
Tyr Ala Lys Val Phe Asp Glu Phe Lys Pro Leu Val Glu Glu Pro Gln Asn Leu Ile Lys  389

CAA AAT TGT GAG CTT TTT GAG CAG CTT GGA GAG TAC AAA TTC CAG AAT GCG CTA TTA GTT
Gln Asn Cys Glu Leu Phe Glu Gln Leu Gly Clu Tyr Lys Phe Gln Asn Ala Leu Leu Val  409
```

FIG. 2B

```
CGT TAC ACC AAG AAA GTA CCC CAA GTG TCA ACT CCA ACT CTT GTA GAG GTC TCA AGA AAC
Arg Tyr Thr Lys Lys Val Pro Gln Val Ser Thr Pro Thr Leu Val Glu Val Ser Arg Asn  429

CTA GGA AAA GTG GGC AGC AAA TGT TGT AAA CAT CCT GAA GCA AAA AGA ATG CCC TGT GCA
Leu Gly Lys Val Gly Ser Lys Cys Cys Lys His Pro Glu Ala Lys Arg Met Pro Cys Ala  449

GAA GAC TAT CTA TCC GTG GTC CTG AAC CAG TTA TGT GTG TTG CAT GAG AAA ACG CCA GTA
Glu Asp Tyr Leu Ser Val Val Leu Asn Gln Leu Cys Val Leu His Glu Lys Thr Pro Val  469

AGT GAC AGA GTC ACC AAA TGC TGC ACA GAA TCC TTG GTG AAC AGG CGA CCA TGC TTT TCA
Ser Asp Arg Val Thr Lys Cys Cys Thr Glu Ser Leu Val Asn Arg Arg Pro Cys Phe Ser  489

GCT CTG GAA GTC GAT GAA ACA TAC GTT CCC AAA GAG TTT AAT GCT GAA ACA TTC ACC TTC
Ala Leu Glu Val Asp Glu Thr Tyr Val Pro Lys Glu Phe Asn Ala Glu Thr Phe Thr Phe  509

CAT GCA GAT ATA TGC ACA CTT TCT GAG AAG GAG AGA CAA ATC AAG AAA CAA ACT GCA CTT
His Ala Asp Ile Cys Thr Leu Ser Glu Lys Glu Arg Gln Ile Lys Lys Gln Thr Ala Leu  529

GTT GAG CTT GTG AAA CAC AAG CCC AAG GCA ACA AAA GAG CAA CTG AAA GCT GTT ATG GAT
Val Glu Leu Val Lys His Lys Pro Lys Ala Thr Lys Glu Gln Leu Lys Ala Val Met Asp  549

GAT TTC GCA GCT TTT GTA GAG AAG TGC TGC AAG GCT GAC GAT AAG GAG ACC TGC TTT GCC
Asp Phe Ala Ala Phe Val Glu Lys Cys Cys Lys Ala Asp Asp Lys Glu Thr Cys Phe Ala  569

                                              MstII
GAG GAG GGT AAA AAA CTT GTT GCT GCA AGT CAA GCT GCC TTA GGC TTA (NNN)p TAA GCTT
Glu Glu Gly Lys Lys Leu Val Ala Ala Ser Gln Ala Ala Leu Gly Leu  (X)p  ***
                                                               PEPTIDE
```

FIG. 2C

```
CC TTA GGC TTA      (NNN)244      TAA GCTT
   Leu Gly Leu (Thr470->Val713) ***
```

FIG. 4A

```
CC TTA GGC TTA      (NNN) 29      TAA GCTT
   Leu Gly Leu (Thr470->Asp498) ***
```

FIG. 4B

```
CC TTA GGC CTC      (NNN)14       TAA GCTT
   Leu Gly Leu (Cys695->Pro708)   ***
           <------ D5 ------>
```

FIG. 4C

```
CC TTA GGC TTA                (NNN)90                  TAA GCTT
   Leu Gly Leu (Thr470->Tyr508,Arg663->Val71 3)   ***
```

FIG. 4D

```
CC TTA GGC TTA ACC TGT GAA GCC TGC CAG GAG CCG GGA GGC CTG GTG GTG CCT CCC ACA
   Leu Gly Leu Thr Cys Glu Ala Cys Gln Glu Pro Gly Gly Leu Val Val Pro Pro Thr   601
      SAH<--- I --->vWF470->713

GAT GCC CCG GTG AGC CCC ACC ACT CTG TAT GTG GAG GAC ATC TCG GAA CCG CCG TTG CAC
Asp Ala Pro Val Ser Pro Thr Thr Leu Tyr Val Glu Asp Ile Ser Glu Pro Pro Leu His   621

GAT TTC TAC TGC AGC AGG CTA CTG GAC CTG GTC TTC CTG CTG GAT GGC TCC TCC AGG CTG
Asp Phe Tyr Cys Ser Arg Leu Leu Asp Leu Val Phe Leu Leu Asp Gly Ser Ser Arg Leu   641

TCC GAG GCT GAG TTT GAA GTG CTG AAG GCC TTT GTG GTG GAC ATG ATG GAG CGG CTG CGC
Ser Glu Ala Glu Phe Glu Val Leu Lys Ala Phe Val Val Asp Met Met Glu Arg Leu Arg   661

ATC TCC CAG AAG TGG GTC CGC GTG GCC GTG GTG GAG TAC CAC GAC GGC TCC CAC GCC TAC
Ile Ser Gln Lys Trp Val Arg Val Ala Val Val Glu Tyr His Asp Gly Ser His Ala Tyr   681

ATC GGG CTC AAG GAC CGG AAG CGA CCG TCA GAG CTG CGG CGC ATT GCC AGC CAG GTG AAG
Ile Gly Leu Lys Asp Arg Lys Arg Pro Ser Glu Leu Arg Arg Ile Ala Ser Gln Val Lys   701
```

FIG. 4E

```
TAT GCG GGC AGC CAG GTG GCC TCC ACC AGC GAG GTC TTG AAA TAC ACA CTG TTC CAA ATC
Tyr Ala Gly Ser Gln Val Ala Ser Thr Ser Glu Val Leu Lys Tyr Thr Leu Phe Gln Ile 721

TTC AGC AAG ATC GAC CGC CCT GAA GCC TCC CGC ATC GCC CTG CTC CTG ATG GCC AGC CAG
Phe Ser Lys Ile Asp Arg Pro Glu Ala Ser Arg Ile Ala Leu Leu Leu Met Ala Ser Gln 741

GAG CCC CAA CGG ATG TCC CGG AAC TTT GTC CGC TAC GTC CAG GGC CTG AAG AAG AAG AAG
Glu Pro Gln Arg Met Ser Arg Asn Phe Val Arg Tyr Val Gln Gly Leu Lys Lys Lys Lys 761

GTC ATT GTG ATC CCG GTG GGC ATT GGG CCC CAT GCC AAC CTC AAG CAG ATC CGC CTC ATC
Val Ile Val Ile Pro Val Gly Ile Gly Pro His Ala Asn Leu Lys Gln Ile Arg Leu Ile 781

GAG AAG CAG GCC CCT GAG AAC AAG GCC TTC GTG CTG AGC AGT GTG GAT GAG CTG GAG CAG
Glu Lys Gln Ala Pro Glu Asn Lys Ala Phe Val Leu Ser Ser Val Asp Glu Leu Glu Gln 801

CAA AGG GAC GAG ATC GTT AGC TAC CTC TGT GAC CTT GCC CCT GAA GCC CCT CCT CCT ACT
Gln Arg Asp Glu Ile Val Ser Tyr Leu Cys Asp Leu Ala Pro Glu Ala Pro Pro Pro Thr 821

CTG CCC CCC GAC ATG GCA CAA GTC TAA GCTT
Leu Pro Pro Asp Met Ala Gln Val ***                                             829
```

FIG. 4F

```
CC TTA GGC TTA AGC AAT GAA CTT CAT CAA GTT CCA TCG AAC TGT GAC TGT CTA AAT GGA
   Leu Gly Leu Ser Asn Glu Leu His Gln Val Pro Ser Asn Cys Asp Cys Leu Asn Gly   601
       SAH<--- I --->UK

GGA ACA TGT GTG TCC AAC AAG TAC TTC TCC AAC ATT CAC TGG TGC AAC TGC CCA AAG AAA
Gly Thr Cys Val Ser Asn Lys Tyr Phe Ser Asn Ile His Trp Cys Asn Cys Pro Lys Lys  621

TTC GGA GGG CAG CAC TGT GAA ATA GAT AAG TCA AAA ACC TGC TAT GAG GGG AAT GGT CAC
Phe Gly Gly Gln His Cys Glu Ile Asp Lys Ser Lys Thr Cys Tyr Glu Gly Asn Gly His  641
                    EGF-LIKE<--- I --->KRINGLE

TTT TAC CGA GGA AAG GCC AGC ACT GAC ACC ATG GGC CGG CCC TGC CTG CCC TGG AAC TCT
Phe Tyr Arg Gly Lys Ala Ser Thr Asp Thr Met Gly Arg Pro Cys Leu Pro Trp Asn Ser  661

GCC ACT GTC CTT CAG CAA ACG TAC CAT GCC CAC AGA TCT GAT GCT CTT CAG CTG GGC CTG
Ala Thr Val Leu Gln Gln Thr Tyr His Ala His Arg Ser Asp Ala Leu Gln Leu Gly Leu  681

GGG AAA CAT AAT TAC TGC AGG AAC CCA GAC AAC CGG AGG CGA CCC TGG TGC TAT GTG CAG
Gly Lys His Asn Tyr Cys Arg Asn Pro Asp Asn Arg Arg Arg Pro Trp Cys Tyr Val Gln  701

GTG GGC CTA AAG CCG CTT GTC CAA GAG TGC ATG GTG CAT GAC TGC GCA GAT GGA AAA TAA
Val Gly Leu Lys Pro Leu Val Gln Glu Cys Met Val His Asp Cys Ala Asp Gly Lys ***  720

GCTT
```

FIG. 8

```
                            ApaI
 CC TTA GGC TTA ACC CCC CTG GGC CCT GCC AGC TCC CTG CCC CAG AGC TTC CTG CTC AAG
    Leu Gly Leu Thr Pro Leu Gly Pro Ala Ser Ser Leu Pro Gln Ser Phe Leu Leu Lys   601
        SAH<--- I --->G-CSF

TGC TTA GAG GAG GTG AGG AAG ATC CAG GGC GAT GGC GCA GCG CTC CAG GAG AAG CTG TGT
Cys Leu Glu Gln Val Arg Lys Ile Gln Gly Asp Gly Ala Ala Leu Gln Glu Lys Leu Cys   621

GCC ACC TAC AAG CTG TGC CAC CCC GAG GAG CTG GTG CTG CTC GGA CAC TCT CTG GGC ATC
Ala Thr Tyr Lys Leu Cys His Pro Glu Glu Leu Val Leu Leu Gly His Ser Leu Gly Ile   641

                        Sstl
CCC TGG GCT CCC CTG AGC TCC TGC CCC AGC CAG GCC CTG CAG CTG GCA GGC TGC TTG AGC
Pro Trp Ala Pro Leu Ser Ser Cys Pro Ser Gln Ala Leu Gln Leu Ala Gly Cys Leu Ser   661

CAA CTC CAT AGC GGC CTT TTC CTC TAC CAG GGG CTC CTG CAG GCC CTG GAA GGG AGA TCC
Gln Leu His Ser Gly Leu Phe Leu Tyr Gln Gly Leu Leu Gln Ala Leu Glu Gly Ile Ser   681

CCC GAG TTG GGT CCC ACC TTG GAC ACA CTG CAG CTG GAC GTC GCC GAC TTT GCC ACC ACC
Pro Glu Leu Gly Pro Thr Leu Asp Thr Leu Gln Leu Asp Val Ala Asp Phe Ala Thr Thr   701

ATC TGG CAG CAG ATG GAA GAA CTG GGA ATG GCC CCT GCC CTG CAG CCC ACC CAG GGT GCC
Ile Trp Gln Gln Met Glu Glu Leu Gly Met Ala Pro Ala Leu Gln Pro Thr Gln Gly Ala   721

ATG CCG GCC TTC GCC TCT GCT TTC CAG CGC CGG GCA GGA GGG GTC CTG GTT GCT AGC CAT
Met Pro Ala Phe Ala Ser Ala Phe Gln Arg Arg Ala Gly Gly Val Leu Val Ala Ser His   741

CTG CAG AGC TTC CTG GAG GTG TCG TAC CGC GTT CTA CGC CAC CTT GCG CAG CCC TGA AGCTT
Leu Gln Ser Phe Leu Glu Val Ser Tyr Arg Val Leu Arg His Leu Ala Gln Pro ***       759
```

FIG. 10

```
AAGCT TTACAACAAA TATAAAAACA ATG AAG TGG GTA ACC TTT ATT TCC CTT CTT TTT CTC TTT
                            Met Lys Trp Val Thr Phe Ile Ser Leu Leu Phe Leu Phe  -12

                                                       ApaI
AGC TCG GCT TAT TCC AGG GGT GTG TTT CGT CGA ACC CCC CTG GGC CCT GCC AGC TCC CTG
Ser Ser Ala Tyr Ser Arg Gly Val Phe Arg Arg Thr Pro Leu Gly Pro Ala Ser Ser Leu    9
                                            I--->G-CSF

CCC CAG AGC TTC CTG CTC AAG TGC TTA GAG CAA GTG AGG AAG ATC CAG GGC GAT GGC GCA
Pro Gln Ser Phe Leu Leu Lys Cys Leu Glu Gln Val Arg Lys Ile Gln Gly Asp Gly Ala   29

GCG CTC CAG GAG AAG CTG TGT GCC ACC TAC AAG CTG TGC CAC CCC GAG GAG CTG GTG CTG
Ala Leu Gln Glu Lys Leu Cys Ala Thr Tyr Lys Leu Cys His Pro Glu Glu Leu Val Leu   49

                                                 SstI
CTC GGA CAC TCT CTG GGC ATC CCC TGG GCT CCC CTG AGC TCC TGC CCC AGC CAG GCC CTG
Leu Gly His Ser Leu Gly Ile Pro Trp Ala Pro Leu Ser Ser Cys Pro Ser Gln Ala Leu   69

CAG CTG GCA GGC TGC TTG AGC CAA CTC CAT AGC GGC CTT TTC CTC TAC CAG GGG CTC CTG
Gln Leu Ala Gly Cys Leu Ser Gln Leu His Ser Gly Leu Phe Leu Tyr Gln Gly Leu Leu   89

CAG GCC CTG GAA GGG ATA TCC CCC GAG TTG GGT CCC ACC TTG GAC ACA CTG CAG CTG GAC
Gln Ala Leu Glu Gly Ile Ser Pro Glu Leu Gly Pro Thr Leu Asp Thr Leu Gln Leu Asp  109

GTC GCC GAC TTT GCC ACC ACC ATC TGG CAG CAG ATG GAA GAA CTG GGA ATG GCC CCT GCC
Val Ala Asp Phe Ala Thr Thr Ile Trp Gln Gln Met Glu Glu Leu Gly Met Ala Pro Ala  129

CTG CAG CCC ACC CAG GGT GCC ATG CCG GCC TTC GCC TCT GCT TTC CAG CGC CGG GCA GGA
Leu Gln Pro Thr Gln Gly Ala Met Pro Ala Phe Ala Ser Ala Phe Gln Arg Arg Ala Gly  149

GGG GTC CTG GTT GCT AGC CAT CTG CAG AGC TTC CTG CAG GTG TCG TAC CGC GTT CTA CGC
Gly Val Leu Val Ala Ser His Leu Gln Ser Phe Leu Glu Val Ser Tyr Arg Val Leu Arg  169
```

FIG. 11A

```
CAC CTT GCG CAG CCC GGT GGA GGC GGT GAT GCA CAC AAG AGT GAG GTT GCT CAT CGG TTT
His Leu Ala Gln Pro Gly Gly Gly Gly Asp Ala His Lys Ser Glu Val Ala His Arg Phe   189
      G-CSF<--- I    linker    I --->SAH

AAA GAT TTG GGA GAA GAA AAT TTC AAA GCC TTG GTG TTG ATT GCC TTT GCT CAG TAT CTT
Lys Asp Leu Gly Glu Glu Asn Phe Lys Ala Leu Val Leu Ile Ala Phe Ala Gln Tyr Leu   209

CAG CAG TGT CCA TTT GAA GAT CAT GTA AAA TTA GTG AAT GAA GTA ACT GAA TTT GCA AAA
Gln Gln Cys Pro Phe Glu Asp His Val Lys Leu Val Asn Glu Val Thr Glu Phe Ala Lys   229

ACA TGT GTT GCT GAT GAG TCA GCT GAA AAT TGT GAC AAA TCA CTT CAT ACC CTT TTT GGA
Thr Cys Val Ala Asp Glu Ser Ala Glu Asn Cys Asp Lys Ser Leu His Thr Leu Phe Gly   249

GAC AAA TTA TGC ACA GTT GCA ACT CTT CGT GAA ACC TAT GGT GAA ATG GCT GAC TGC TGT
Asp Lys Leu Cys Thr Val Ala Thr Leu Arg Glu Thr Tyr Gly Glu Met Ala Asp Cys Cys   269

GCA AAA CAA GAA CCT GAG AGA AAT GAA TGC TTC TTG CAA CAC AAA GAT GAC AAC CCA AAC
Ala Lys Gln Glu Pro Glu Arg Asn Glu Cys Phe Leu Gln His Lys Asp Asp Asn Pro Asn   289

CTC CCC CGA TTG GTG AGA CCA GAG GTT GAT GTG ATG TGC ACT GCT TTT CAT GAC AAT GAA
Leu Pro Arg Leu Val Arg Pro Glu Val Asp Val Met Cys Thr Ala Phe His Asp Asn Glu   309

GAG ACA TTT TTG AAA AAA TAC TTA TAT GAA ATT GCC AGA AGA CAT CCT TAC TTT TAT GCC
Glu Thr Phe Leu Lys Lys Tyr Leu Tyr Glu Ile Ala Arg Arg His Pro Tyr Phe Tyr Ala   329

CCG GAA CTC CTT TTC TTT GCT AAA AGG TAT AAA GCT GCT TTT ACA GAA TGT TGC CAA GCT
Pro Glu Leu Leu Phe Phe Ala Lys Arg Tyr Lys Ala Ala Phe Thr Glu Cys Cys Gln Ala   349

GCT GAT AAA GCT GCC TGC CTG TTG CCA AAG CTC GAT GAA CTT CGG GAT GAA GGG AAG GCT
Ala Asp Lys Ala Ala Cys Leu Leu Pro Lys Leu ASP Glu Leu Arg Asp Glu Gly Lys Ala   369

TCG TCT GCC AAA CAG AGA CTC AAG TGT GCC AGT CTC CAA AAA TTT GGA GAA AGA GCT TTC
Ser Ser Ala Lys Gln Arg Leu Lys Cys Ala Ser Leu Gln Lys Phe Gly Glu Arg Ala Phe   389
```

FIG. 11B

```
AAA GCA TGG GCA GTA GCT CGC CTG AGC CAG AGA TTT CCC AAA GCT GAG TTT GCA GAA GTT
Lys Ala Trp Ala Val Ala Arg Leu Ser Gln Arg Phe Pro Lys Ala Glu Phe Ala Glu Val   409

TCC AAG TTA GTG ACA GAT CTT ACC AAA GTC CAC ACG GAA TGC TGC CAT GGA GAT CTG CTT
Ser Lys Leu Val Thr Asp Leu Thr Lys Val His Thr Glu Cys Cys His Gly Asp Leu Leu   429

GAA TGT GCT GAT GAC AGG GCG GAC CTT GCC AAG TAT ATC TGT GAA AAT CAA GAT TCG ATC
Glu Cys Ala Asp Asp Arg Ala Asp Leu Ala Lys Tyr Ile Cys Glu Asn Gln Asp Ser Ile   449

TCC AGT AAA CTG AAG GAA TGC TGT GAA AAA CCT CTG TTG GAA AAA TCC CAC TGC ATT GCC
Ser Ser Lys Leu Lys Glu Cys Cys Glu Lys Pro Leu Leu Glu Lys Ser His Cys Ile Ala   469

GAA GTG GAA AAT GAT GAG ATG CCT GCT GAC TTG CCT TCA TTA GCT GCT GAT TTT GTT GAA
Glu Val Glu Asn Asp Glu Met Pro Ala Asp Leu Pro Ser Leu Ala Ala Asp Phe Val Glu   489

AGT AAG GAT GTT TGC AAA AAC TAT GCT GAG GCA AAG GAT GTC TTC CTG GGC ATG TTT TTG
Ser Lys Asp Val Cys Lys Asn Tyr Ala Glu Ala Lys Asp Val Phe Leu Gly Met Phe Leu   509

TAT GAA TAT GCA AGA AGG CAT CCT GAT TAC TCT GTC GTA CTG CTG CTG AGA CTT GCC AAG
Tyr Glu Tyr Ala Arg Arg His Pro Asp Tyr Ser Val Val Leu Leu Leu Arg Leu Ala Lys   529

ACA TAT GAA ACC ACT CTA GAG AAG TGC TGT GCC GCT GCA GAT CCT CAT GAA TGC TAT GCC
Thr Tyr Glu Thr Thr Leu Glu Lys Cys Cys Ala Ala Ala Asp Pro His Glu Cys Tyr Ala   549

AAA GTG TTC GAT GAA TTT AAA CCT CTT GTG GAA GAG CCT CAG AAT TTA ATC AAA CAA AAT
Lys Val Phe Asp Glu Phe Lys Pro Leu Val Glu Glu Pro Gln Asn Leu Ile Lys Gln Asn   569

TGT GAG CTT TTT GAG CAG CTT GGA GAG TAC AAA TTC CAG AAT GCG CTA TTA GTT CGT TAC
Cys Glu Leu Phe Glu Gln Leu Gly Glu Tyr Lys Phe Gln Asn Ala Leu Leu Val Arg Tyr   589

ACC AAG AAA GTA CCC CAA GTG TCA ACT CCA ACT CTT GTA GAG GTC TCA AGA AAC CTA GGA
Thr Lys Lys Val Pro Gln Val Ser Thr Pro Thr Leu Val Glu Val Ser Arg Asn Leu Gly   609
```

FIG. 11C

```
AAA GTG GGC AGC AAA TGT TGT AAA CAT CCT GAA GCA AAA AGA ATG CCC TGT GCA GAA GAC
Lys Val Gly Ser Lys Cys Cys Lys His Pro Glu Ala Lys Arg Met Pro Cys Ala Glu Asp   629

TAT CTA TCC GTG GTC CTG AAC CAG TTA TGT GTG TTG CAT GAG AAA ACG CCA GTA AGT GAC
Tyr Leu Ser Val Val Leu Asn Gln Leu Cys Val Leu His Glu Lys Thr Pro Val Ser Asp   649

AGA GTC ACC AAA TGC TGC ACA GAA TCC TTG GTG AAC AGG CGA CCA TGC TTT TCA GCT CTG
Arg Val Thr Lys Cys Cys Thr Glu Ser Leu Val Asn Arg Arg Pro Cys Phe Ser Ala Leu   669

GAA GTC GAT GAA ACA TAC GTT CCC AAA GAG TTT AAT GCT GAA ACA TTC ACC TTC CAT GCA
Glu Val Asp Glu Thr Tyr Val Pro Lys Glu Phe Asn Ala Glu Thr Phe Thr Phe His Ala   689

GAT ATA TGC ACA CTT TCT GAG AAG GAG AGA CAA ATC AAG AAA CAA ACT GCA CTT GTT GAG
Asp Ile Cys Thr Leu Ser Glu Lys Glu Arg Gln Ile Lys Lys Gln Thr Ala Leu Val Glu   709

CTT GTG AAA CAC AAG CCC AAG GCA ACA AAA GAG CAA CTG AAA GCT GTT ATG GAT GAT TTC
Leu Val Lys His Lys Pro Lys Ala Thr Lys Glu Gln Leu Lys Ala Val Met Asp Asp Phe   729

GCA GCT TTT GTA GAG AAG TGC TGC AAG GCT GAC GAT AAG GAG ACC TGC TTT GCC GAG GAG
Ala Ala Phe Val Glu Lys Cys Cys Lys Ala Asp Asp Lys Glu Thr Cys Phe Ala Glu Glu   749

                                            MstII
GGT AAA AAA CTT GTT GCT GCA AGT CAA GCT GCC TTA GGC TTA TAA CATCACATTT
Gly Lys Lys Leu Val Ala Ala Ser Gln Ala Ala Leu Gly Leu ***                       763

AAAAGCATCT CAGCCTACCA TGAGAATAAG AGAAAGAAAA TGAAGATCAA AAGCTT
```

FIG. 11D

```
CC TTA GGC TTA CAG GTG CAG CTC GAG CAG TCT GGA CCT GAG CTG GTG AAG CCT GGG GCC
   Leu Gly Leu Gln Val Gln Leu Glu Gln Ser Gly Pro Glu Leu Val Lys Pro Gly Ala   601
       SAH< --- I--->VH

TCA GTG AAG ATT TCC TGC AAA GCT TCT GGC TAC GCA TTC AGT AGG TCT TGG ATG AAC TGG
Ser Val Lys Ile Ser Cys Lys Ala Ser Gly Tyr Ala Phe Ser Arg Ser Trp Met Asn Trp   621

GTG AAG CAG AGG CCT GGA CAG GGT CTT GAG TGG ATT GGA CGG ATT TAT CCT GGA GAT GGA
Val Lys Gln Arg Pro Gly Gln Gly Leu Glu Trp Ile Gly Arg Ile Tyr Pro Gly Asp Gly   641

GAT ACC AAA TAC AAT GGG AAG TTC AAG GGC AAG GCC ACA CTG ACT GCG GAC AGA TCA TCC
Asp Thr Lys Tyr Asn Gly Lys Phe Lys Gly Lys Ala Thr Leu Thr Ala Asp Arg Ser Ser   661

AGC ACA GCC TAC ATG CAG CTC AGC AGC CTG ACC TCT GTG GGC TCT GCG GTC TAT TTC TGT
Ser Thr Ala Tyr Met Gln Leu Ser Ser Leu Thr Ser Val Gly Ser Ala Val Tyr Phe Cys   681

GCA AAA GAG AAC AAT AGG TTC GAC GAG AGG GGT TAC TAT GCT ATG GAC TAC TGG GGC CAA
Ala Lys Glu Asn Asn Arg Phe Asp Glu Arg Gly Tyr Tyr Ala Met Asp Tyr Trp Gly Gln   701

GGG ACC ACG GTC ACC GTC TCC TCA GGT GGC GGT GGC TCG GGC GGT GGT GGG TCG GGT GGC
Gly Thr Thr Val Thr Val Ser Ser Gly Gly Gly Gly Ser Gly Gly Gly Gly Ser Gly Gly   721
                         VH< --- I                Synthetic linker
```

FIG. 14A

```
GGC GGA TCT AAC ATT CAG TTG ACC CAG TCT CCA AAT TCC ATG TCC ACA TCA GTA GGA GAC
Gly Gly Ser Asn Ile Gln Leu Thr Gln Ser Pro Asn Ser Met Ser Thr Ser Val Gly Asp  741
            I--->VL

AGG GTC AGC ATC ACC TGC AAG GCC AGT CAG GAT GTG GAT ACT TCT GTA GCC TGG TAT CAA
Arg Val Ser Ile Thr Cys Lys Ala Ser Gln Asp Val Asp Thr Ser Val Ala Trp Tyr Gln  761

CAG AAA CCA GGG CAA TCT CCT AAA CTA CTG ATT TAC TGG GCA TCC ACC CGG CAC ACT GGA
Gln Lys Pro Gly Gln Ser Pro Lys Leu Leu Ile Tyr Trp Ala Ser Thr Arg His Thr Gly  781

GTC CCT GAT CGC TTC ACA GGC AGT GGA TCT GGG ACA GAT TTC ACT CTC ACC ATT AGC AAT
Val Pro Asp Arg Phe Thr Gly Ser Gly Ser Gly Thr Asp Phe Thr Leu Thr Ile Ser Asn  801

GTG CAG TCT GAA GAC TCG GCA GAT TAT TTC TGT CAG CAA TAT AGC AGC TAT CCG TGG ACG
Val Gln Ser Glu Asp Ser Ala Asp Tyr Phe Cys Gln Gln Tyr Ser Ser Tyr Pro Trp Thr  821

TTC GGT GGA GGG ACC AAG CTG GAG ATC AAA TAA GCTT
Phe Gly Gly Gly Thr Lys Leu Glu Ile Lys ***                                      831
```

FIG. 14B

| PRODUCT | $IC_{50}$ (nM) |
|---|---|
| RG12986 | 50 |
| HSA-vWF 694-708 | 50000 |
| HSA-vWF 470-713 C471,474→G | 20 |
| HSA-vWF 470-704 C471,474→G | <10 |

FUSION POLYPEPTIDES COMPRISING HUMAN SERUM ALBUMIN, NUCLEIC ACIDS ENCODING SAME, AND RECOMBINANT EXPRESSION THEREOF

This is a continuation of application No. 08/256,927, filed on Jul. 28, 1994, now abandoned, which is a national stage application of PCT/FR93/00085; filed Jan. 28, 1993, which is a priority application based on French Application 92-01064, filed Jan. 31, 1992.

The present invention relates to new biologically active polypeptides, their preparation and pharmaceutical compositions containing them.

More particularly, the present invention relates to essentially recombinant polypeptides composed of an active part derived from a natural or artificial polypeptide having a therapeutic activity and coupled to an albumin or to a variant of albumin. It is understood that the therapeutic activity of the polypeptides of the invention can be either direct (treatment of diseases), or indirect (and for example capable of being used in the prevention of diseases, in the design of vaccines, in medical imaging techniques and the like).

It is understood in the following text that the albumin variants designate any protein with a high plasma half-life which is obtained by modification (mutation, deletion and/or addition), by genetic engineering techniques, of a gene encoding a given isomorph of human serum albumin, as well as any macromolecule with a high plasma half-life obtained by in vitro modification of the protein encoded by such genes. Albumin being highly polymorphic, numerous natural variants have been identified and classified [Weitkamp L. R. et al., Ann. Hum. Genet. 37 (1973) 219].

The aim of the present invention is to prepare artificial proteins which are biologically active and can be used pharmaceutically. Indeed, numerous polypeptides possessing one or more potential therapeutic activities cannot be exploited pharmaceutically. This may have various reasons, such as especially their low stability in vivo, their complex or fragile structure, the difficulty of producing them on an industrially acceptable scale and the like. Likewise, some polypeptides do not give the expected results in vivo because of problems of administration, of packaging, of pharmacokinetics and the like.

The present invention makes it possible to overcome these disadvantages. The present invention indeed provides new molecules which permit an optimal therapeutic exploitation of the biological properties of these polypeptides. The present invention results especially from the demonstration that it is possible to couple genetically any active structure derived from a biologically active polypeptide to another protein structure consisting of albumin, without impairing the said biological properties thereof. It also results from the demonstration by the Applicant that human serum albumin makes it possible efficiently to present the active structure to its sites for interaction, and that it provides a high plasma stability for the polypeptide of the invention. The polypeptides of the invention thus make it possible to maintain, in the body, a given biological activity for a prolonged period. They thus make it possible to reduce the administered doses and, in some cases, to potentiate the therapeutic effect, for example by reducing the side effects following a higher administration. The polypeptides of the invention make it possible, in addition, to generate and to use structures derived from biologically active polypeptides which are very small and therefore very specific for a desired effect. It is understood that the peptides having a biological activity, which are of therapeutic interest, may also correspond to non-natural peptide sequences isolated for example from random peptide libraries. The polypeptides of the invention possess, moreover, a particularly advantageous distribution in the body, which modifies their pharmacokinetic properties and favours the development of their biological activity and their use. In addition, they also have the advantage of being weakly or non-immunogenic for the organism in which they are used. Finally, the polypeptides of the invention can be expressed (and preferentially secreted) by recombinant organisms, at levels permitting their industrial exploitation.

One subject of the present invention therefore relates to polypeptides containing an active part derived from a polypeptide having a therapeutic activity, coupled to an albumin or a variant of albumin.

In a specific embodiment, the peptides possessing a therapeutic activity are not of human origin. For example, there may be mentioned peptides, or their derivatives, possessing properties which are potentially useful in the pathologies of the blood and interstitial compartments, such as hirudin, trigramine, antistatine, tick anticoagulant peptides (TAP), arietin, applagin and the like.

More particularly, in the molecules of the invention, the polypeptide having a therapeutic activity is a polypeptide of human origin or a molecular variant. For example, this may be all or part of an enzyme, an enzyme inhibitor, an antigen, an antibody, a hormone, a factor involved in the control of coagulation, an interferon, a cytokine [the interleukins, but also their variants which are natural antagonists of their binding to the receptor(s), the SIS (small induced secreted) type cytokines and for example the macrophage inflammatory proteins (MIPs), and the like], of a growth factor and/or of differentiation [and for example the transformant growth factors (TGFs), the blood cell differentiation factors (erythropoietin, M-CSF, G-CSF, GM-CSF and the like), insulin and the growth factors resembling it (IGFs), or alternatively cell permeability factors (VPF/VEGF), and the like], of a factor involved in the genesis/resorption of bone tissues (OIF and osteospontin for example), of a factor involved in cellular motility or migration [and for example autocrine motility factor (AMF), migration stimulating factor (MSF), or alternatively the scatter factor (scatter factor/hepatocyte growth factor)], of a bactericidal or antifungal factor, of a chemotactic factor [and for example platelet factor 4 (PF4), or alternatively the monocyte chemoattracting peptides (MCP/MCAF) or neutrophil chemoattracting peptides (NCAF), and the like], of a cytostatic factor (and for example the proteins which bind to galactosides), of a plasma (and for example von Willebrand factor, fibrinogen and the like) or interstitial (laminin, tenascin, vitronectin and the like) adhesive molecule or extracellular matrices, or alternatively any peptide sequence which is an antagonist or agonist of molecular and/or intercellular interactions involved in the pathologies of the circulatory and interstitial compartments and for example the formation of arterial and venous thrombi, cancerous metastases, tumour angiogenesis, inflammatory shock, autoimmune diseases, bone and osteoarticular pathologies and the like.

The active part of the polypeptides of the invention may consist for example of the polypeptide having a whole therapeutic activity, or of a structure derived therefrom, or alternatively of a non-natural polypeptide isolated from a peptide library. For the purposes of the present invention, a derived structure is understood to mean any polypeptide obtained by modification and preserving a therapeutic activity. Modification should be understood to mean any mutation, substitution, deletion, addition or modification of genetic and/or chemical nature. Such derivatives may be generated for various reasons, such as especially that of increasing the affinity of the molecule for its binding sites, that of improving its levels of production, that of increasing its resistance to proteases, that of increasing its therapeutic efficacy or alternatively of reducing its side effects, or that of conferring on it new biological properties. As an example, the chimeric polypeptides of the invention possess pharmacokinetic properties and a biological activity which can be used for the prevention or treatment of diseases.

Particularly advantageous polypeptides of the invention are those in which the active part has:

(a) the whole peptide structure or, (b) a structure derived from (a) by structural modification (mutation, substitution addition and/or deletion of one or more residues) and possessing a therapeutic activity.

Among the structures of the (b) type, there may be mentioned more particularly the molecules in which certain N- or O-glycosylation sites have been modified or suppressed, the molecules in which one or more residues have been substituted, or the molecules in which all the cystein residues have been substituted. There may also be mentioned molecules obtained from (a) by deletion of regions not involved or not highly involved in the interaction with the binding sites considered, or expressing an undesirable activity, and molecules containing, compared to (a), additional residues such as for example an N-terminal methionine and/or a signal for secretion and/or a joining peptide.

The active part of the molecules of the invention can be coupled either directly or via an artificial peptide to albumin. Furthermore, it may constitute the N-terminal end as well as the C-terminal end of the molecule. Preferably, in the molecules of the invention, the active part constitutes the C-terminal part of the chimera. It is also understood that the biologically active part may be repetitive within the chimera. A schematic representation of the molecules of the invention is given in FIG. 1.

Another subject of the invention relates to a process for preparing the chimeric molecules described above. More specifically, this process consists in causing a eukaryotic or prokaryotic cellular host to express a nucleotide sequence encoding the desired polypeptide, and then in harvesting the polypeptide produced.

Among the eukaryotic hosts which can be used within the framework of the present invention, there may be mentioned animal cells, yeasts or fungi. In particular, as regards yeasts, there may be mentioned yeasts of the genus Saccharomyces, Kluyveromyces, Pichia, Schwanniomyces, or Hansenula. As regards animal cells, there may be mentioned COS, CHO and C127 cells and the like. Among the fungi capable of being used in the present invention, there may be mentioned more particularly Aspergillus ssp, or Trichoderma ssp. As prokaryotic hosts, the use of bacteria such as *Escherichia coli,* or belonging to the genera Corynebacterium, Bacillus, or Streptomyces is preferred.

The nucleotide sequences which can be used within the framework of the present invention can be prepared in various ways. Generally, they are obtained by assembling, in reading phase, the sequences encoding each of the functional parts of the polypeptide. The latter may be isolated by the techniques of persons skilled in the art, and for example directly from cellular messenger RNAs (mRNAs), or by recloning from a complementary DNA (cDNA) library, or alternatively they may be completely synthetic nucleotide sequences. It is understood, furthermore, that the nucleotide sequences may also be subsequently modified, for example by the techniques of genetic engineering, in order to obtain derivatives or variants of the said sequences.

More preferably, in the process of the invention, the nucleotide sequence is part of an expression cassette comprising a region for initiation of transcription (promoter region) permitting, in the host cells, the expression of the nucleotide sequence placed under its control and encoding the polypeptides of the invention. This region may come from promoter regions of genes which are highly expressed in the host cell used, the expression being constitutive or regulatable. As regards yeasts, it may be the promoter of the gene for phosphoglycerate kinase (PGK), glyceraldehyde-3-phosphate dehydrogenase (GPD), lactase (LAC4), enolases (ENO), alcohol dehydrogenases (ADH), and the like. As regards bacteria, it may be the promoter of the right-hand or left-hand genes from the lambda bacteriophage ($P_L$, $P_R$), or alternatively the promoters of the genes for the tryptophan ($P_{trp}$) or lactose ($P_{lac}$) operons. In addition, this control region can be modified, for example by in vitro mutagenesis, by the introduction of additional control elements or of synthetic sequences, or by deletions or substitutions of the original control elements. The expression cassette may also comprise a region for termination of transcription which is functional in the host envisaged, positioned immediately downstream of the nucleotide sequence encoding a polypeptide of the invention.

In a preferred mode, the polypeptides of the invention result from the expression, in a eukaryotic or prokaryotic host, of a nucleotide sequence and from the secretion of the product of expression of the said sequence into the culture medium. It is indeed particularly advantageous to be able to obtain, by the recombinant route, molecules directly in the culture medium. In this case, the nucleotide sequence encoding a polypeptide of the invention is preceded by a "leader" sequence (or signal sequence) directing the nascent polypeptide in the secretory pathways of the host used. This "leader" sequence may be the natural signal sequence of the biologically active polypeptide in the case where the latter is a naturally secreted protein, or that of the stabilizing structure, but it may also be any other functional "leader" sequence, or an artificial "leader" sequence. The choice of one or the other of these sequences is especially guided by the host used. Examples of functional signal sequences include those of the genes for the sexual pheromones or the "killer" toxins of yeasts.

In addition to the expression cassette, one or several markers which make it possible to select the recombinant host may be added, such as for example the URA3 gene from the yeast *S. cerevisiae,* or genes conferring the resistance to antibiotics such as geneticin (G418) or to any other toxic compound such as certain metal ions.

The unit formed by the expression cassette and by the selectable marker can be introduced directly into the considered host cells, or previously inserted in a functional self-replicating vector. In the first case, sequences homologous to regions present in the genome of the host cells are preferably added to this unit; the said sequences then being positioned on each side of the expression cassette and of the selectable gene so as to increase the frequency of integration of the unit into the genome of the host by targetting the integration of the sequences by homologous recombination. In the case where the expression cassette is inserted in a replicative system, a preferred replication system for yeasts of the genus Kluyveromyces is derived from the plasmid pKD1 originally isolated from *K. drosophilarum;* a preferred replication system for yeasts of the genus Saccharomyces is derived from the 2$\mu$ plasmid from *S. cerevisiae.* Furthermore, this expression plasmid may contain all or part of the said replication systems, or may combine elements derived both from the plasmid pKD1 and the 2$\mu$ plasmid.

In addition, the expression plasmids may be shuttle vectors between a bacterial host such as *Escherichia coli* and the chosen host cell. In this case, a replication origin and a selectable marker functioning in the bacterial host are required. It is also possible to position restriction sites surrounding the bacterial and unique sequences on the expression vector: this makes it possible to suppress these sequences by cutting and religation in vitro of the truncated vector before transformation of the host cells, which may result in an increase in the number of copies and in an increased stability of the expression plasmids in the said hosts. For example, such restriction sites may correspond to sequences such as 5'-GGCCNNNNNGGCC-3' SEQ ID NO:19 (SfiI) or 5'-GCGGCCGC-3' (NotI) in so far as these sites are extremely rare and generally absent from an expression vector.

After construction of such vectors or expression cassette, the latter are introduced into the host cells selected according to the conventional techniques described in the literature. In this respect, any method permitting the introduction of a foreign DNA into a cell can be used. This may be especially transformation, electroporation, conjugation, or any other technique known to persons skilled in the art. As an example of yeast-type hosts, the various strains of Kluyveromyces used were transformed by treating the whole cells in the presence of lithium acetate and polyethylene glycol, according to the technique described by Ito et al. [J. Bacteriol. 153 (1983) 163]. The transformation technique described by Durrens et al. [Curr. Genet. 18 (1990) 7] using ethylene glycol and dimethyl sulphoxide was also used. It is also possible to transform the yeasts by electroporation, according to the method described by Karube et al. [FEBS Letters 182 (1985) 90]. An alternative procedure is also described in detail in the examples below.

After selection of the transformed cells, the cells expressing the said polypeptides are inoculated and the recovery of the said polypeptides can be carried out, either during the cell growth for the "continuous" processes, or at the end of growth for the "batch" cultures. The polypeptides which are the subject of the present invention are then purified from the culture supernatant for their molecular, pharmacokinetic and biological characterization.

A preferred expression system for the polypeptides of the invention consists in using yeasts of the genus Kluyveromyces as host cell, transformed by certain vectors derived from the extrachromosomal replicon pKD1 originally isolated from *K. marxianus* var. drosophilarum. These yeasts, and in particular *K. lactis* and *K. fragilis* are generally capable of stably replicating the said vectors and possess, in addition, the advantage of being included in the list of G.R.A.S. ("Generally Recognized As Safe") organisms. Favoured yeasts are preferably industrial yeasts of the genus Kluyveromyces which are capable of stably replicating the said plasmids derived from the plasmid pKD1 and in which has been inserted a selectable marker as well as an expression cassette permitting the secretion, at high levels, of the polypeptides of the invention.

The present invention also relates to the nucleotide sequences encoding the chimeric polypeptides described above, as well as the eukaryotic or prokaryotic recombinant cells comprising such sequences.

The present invention also relates to the application, as medicinal products, of the polypeptides according to the present invention. More particularly, the subject of the invention is any pharmaceutical composition comprising one or more polypeptides or nucleotide sequences as described above. The nucleotide sequences can indeed be used in gene therapy.

The present invention will be more fully described with the aid of the following examples, which should be considered as illustrative and non-limiting.

BRIEF DESCRIPTION OF THE DRAWINGS

The representations of the plasmids indicated in the following figures are not plotted to scale and only the restriction sites important for the understanding of the clonings carried out have been indicated.

FIGS. 2(a) and 2(b), together, comprise an example of a nucleotide sequence (SEQ ID NO:1) and an amino acid sequence (SEQ ID NO:2) of a HindIII restriction fragment encoding a chimeric protein of the prepro-HSA-PEPTIDE type. The black arrows indicate the end of the "pre" and "pro" regions of HSA. The MstII restriction site is underligned and the codon specifying the termination of translation is in bold characters.

FIGS. 4A, 4B, 4C, 4D, and 4E collectively show examples of nucleotide sequences of MstII-HindIII restriction fragments derived from the von Willebrand factor. FIG. 4A is a representation of the structure of the MstII-HindIII fragment of the plasmid pYG1248 (SEQ ID NOS:3 and 4). FIG. 4B is a representation of the structure of the MstII-HindIII fragment of the plasmid pYG1214 (SEQ ID NOS:5 and 6). FIG. 4C is a representation of the MstII-HindIII fragment of the plasmid pYG1206; in this particular chimera, the Leu694 residue of the vWF is also the last residue (Leu585) of the HSA. FIG. 4D is a representation of the MstII-HindIII fragment of the plasmid pYG1223 (SEQ ID NOS:9 and 10). The numbering of the amino acids corresponds to the numbering of the mature vWF according to Titani et al. [Biochemistry 25 (1986) 3171–3184]. The MstII and HindIII restriction sites are underlined and the translation termination codon is in bold characters. FIG. 4E is a nucleotide sequence (SEQ ID NO:3) of the MstII-HindIII restriction fragment of the plasmid pYG1248. The numbering of the amino acids (right-hand column) corresponds to the mature chimeric protein HSA-vWF470→713 (829 residues). The Thr470, Leu494, Asp498, Pro502, Tyr508, Leu694, Pro704 and Pro708 residues of the mature vWF are underlined.

FIG. 5A shows the results of coomassie blue staining of a molecular weight standard (lane 2); of a supernatant equivalent to 50 μl of the culture transformed with the plasmid pKan707 in YPL medium (lane 1); the plasmid pYG1248 in YPD medium (lane 3) and the plasmid pYG1248 in YPL medium (lane 4).

FIG. 5B shows the results of immunological characterization of the secreted material after using mouse antibodies directed against human vWF. The lanes are the same as described for FIG. 5A except that biotinilated molecular weight standards were used (lane 2).

FIG. 5C shows the results of immunological characterization of the secreted material after using rabbit antibodies directed against human albumin: supernatant equivalent to 50 μl of the culture transformed with the plasmid pKan707 in YPL medium (lane 1), the plasmid pYG1248 in YPD medium (lane 2) the plasmid pYG1248 in YPL medium (lane 3).

In FIG. 6A, coomassie blue staining was employed. Lane 1 is the molecular weight standard, lane 2 is the supernatant equivalent to 2.5 μl of a "Fed Batch" culture in YPD medium after 24 hours of growth; lane 3 is the supernatant of the same culture after 40 hours; and lane 4 is the supernatant of the same culture after 46 hours of growth.

FIG. 6B shows the results of immunological characterization of the secreted material after using mouse antibodies directed against the human vWF. The lanes are the same as in FIG. 6A except that biotinilated molecular weight standards were used.

FIG. 8: Nucleotide sequence (SEQ ID NO:11) and amino acid sequence (SEQ ID NO:12) of the MstII-HindIII restriction fragment of the plasmid pYG1341 (HSA-UK1→135). The limit of the EGF-like domain (UK1→46) present in the MstII-HindIII restriction fragment of the plasmid pYG1340 is indicated. The numbering of the amino acids corresponds to the mature chimeric protein SAU-UK1→135 (720 residues).

FIG. 10: Nucleotide sequence (SEQ ID NO:13) and amino acid sequence (SEQ ID NO:14) of the MstII-HindIII restriction fragment of the plasmid pYG1259 (HSA-G.CSF). The limit of the G-CSF part (174 residues) is indicated. The ApaI and SstI (SstI) restriction sites are underlined. The numbering of the amino acids corresponds to the mature chimeric protein HSA-G.CSF (759 residues).

FIG. 11(*a*) and 11(*b*) together comprise the nucleotide sequence (SEQ ID NO:15) and amino acid sequence (SEQ ID NO:16) of the HindIII restriction fragment of the plasmid pYG1301 (chimera G.CSF-$Gly_4$-HSA). The black arrows indicate the end of the "pre" and "pro" regions of HSA. The ApaI, SstI (SacI) and MstII restriction sites are underlined. The G.CSF (174 residues) and HSA (585 residues) domains are separated by the synthetic linker GGGG. The numbering of the amino acids corresponds to the mature chimeric protein G.CSF-Gly4-SAH (763 residues). The nucleotide sequence between the translation termination codon and the HindIII site comes from the HSA complementary DNA (cDNA) as described in Patent Application EP 361 991.

FIG. 12A shows the results of coomassie blue staining of a molecular weight standard (lane 2); supernatant equivalent to 100 μl of culture transformed with the plasmid pKan707 in YPL medium (lane 1); the plasmid pYG1266 in YPD medium (lane 3) and the plasmid pYG1266 in YPL medium (lane 4).

FIG. 12B shows the results of immunological characterization of the material secreted after using primary antibodies directed against human G-CSF. The lanes are as described above for FIG. 12A.

FIG. 12C shows the results of immunological characterization of the material secreted after using primary antibodies directed against human albumin. The lanes are as described above for FIG. 12A.

FIG. 13A shows the results of coomassie blue staining of a supernatant equivalent to 100 μl of the culture transformed with the plasmid pYG1303 (lane 1), the plasmid pYG1267 (lane 2), and the plasmid pYG1352 (lane 3). Lane 4 is the molecular weight standard.

B, immunological characterization of the material secreted after using primary antibodies directed against the human G-CSF: same legend as in A.

FIG. 14: Nucleotide sequence (SEQ ID NO:17) and amino acid sequence (SEQ ID NO:18) of the MstII-HindIII restriction fragment of the plasmid pYG1382 (HSA-Fv'). The VH (124 residues) and VL (107 residues) domains of the Fv' fragment are separated by the synthetic linker $(GGGGS)_{x3}$. The numbering of the amino acids corresponds to the mature chimeric protein HSA-Fv' (831 residues).

Figures 15A, 15B:
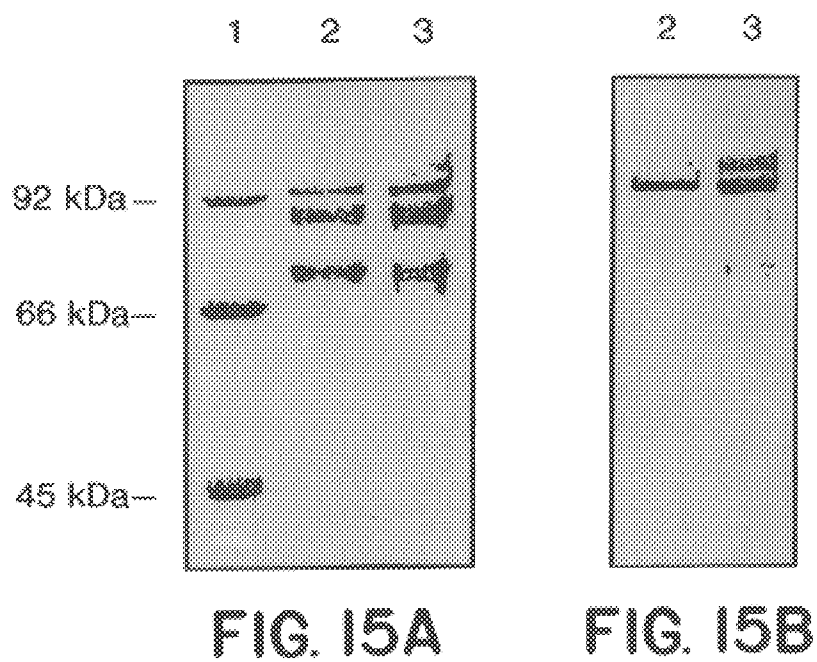

FIGS. 15A and 15B collectively show the characterization of the secretions of the chimera HSA-Fv' by the strain CBS 293.91 transformed with the plasmid pYG1383 (LAC4) after 4 days of growth in erlenmeyers at 28° C. in YPD medium (lane 2), and in YPL medium (lane 3). Lane 1 shows the molecular weight standard. The deposits, equivalent to 200 μl of culture (precipitation with ethanol), are run on a PAGE-SDS gel (8.5%).

FIG. 15A shows the results of coomassie blue staining of the gel.

FIG. 15B shows the results of immunological characterization of the material secreted after using primary antibodies directed against HSA.

Figures 16, 17:
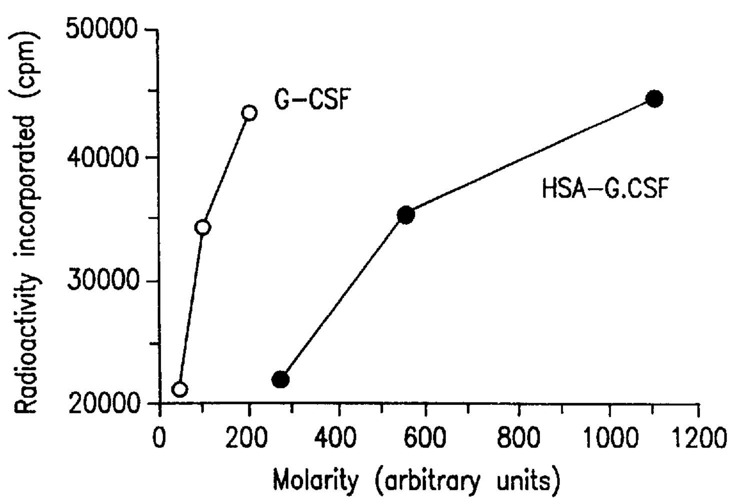

FIG. 16: Assay of the in vitro antagonistic activity of the agglutination of human platelets fixed with formaldehyde: IC50 of the hybrids HSA-vWF694–708, [HSA-vWF470–713 C471G, C474G] and [HSA-vWF470–704 C471G, C474G] compared with the standard RG12986. The determination of the dose-dependent inhibition of the platelet agglutination is carried out according to the method described by C. Prior et al. [Bio/Technology (1992) 10 66] using an aggregameter recording the variations in optical transmission, with stirring, at 37° C. in the presence of human vWF, botrocetin (8.2 mg/ml) of the test product at various dilutions. The concentration of the product which makes it possible to inhibit the control agglutination (in the absence of product) by half is then determined (IC50).

FIG. 17: Activity on the in vitro cellular proliferation of the murine line NFS60. The radioactivity ($^3$H-thymidine) incorporated into the cellular nuclei after 6 hours of incubation is represented on the y-axis (cpm); the quantity of product indicated on the x-axis is expressed in molarity (arbitrary units).

Figure 18:
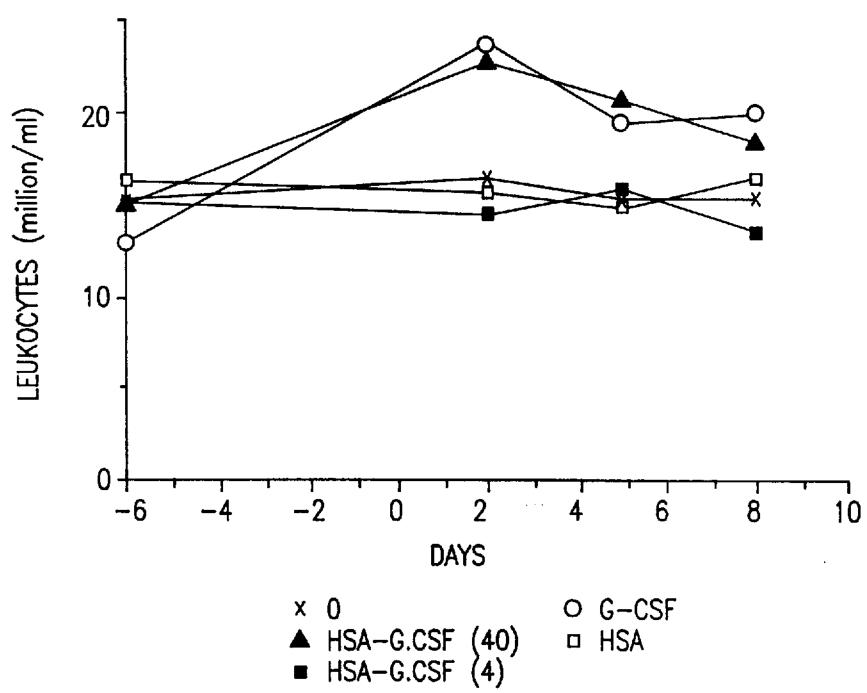

FIG. 18: Activity on granulopoiesis in vivo in rats. The number of neutrophils (average for 7 animals) is indicated on the y-axis as a function of time. The products tested are the chimera HSA-G.CSF (pYG1266), 4 or 40 mg/rat/day), the reference G-CSF (10 mg/rat/day), the recombinant HSA purified from *Kluyveromyces lactis* supernatant (HSA, 30 mg/rat/day, cf. EP 361 991), or physiological saline.

EXAMPLES

GENERAL CLONING TECHNIQUES

The methods conventionally used in molecular biology, such as the preparative extractions of plasmid DNA, the centrifugation of plasmid DNA in caesium chloride gradient, electrophoresis on agarose or acrylamide gels, purification of DNA fragments by electroelution, extractions of proteins with phenol or phenol-chloroform, DNA precipitation in saline medium with ethanol or isopropanol, transformation in *Escherichia coli,* and the like are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were provided by New England Biolabs (Biolabs), Bethesda Research Laboratories (BRL) or Amersham and are used according to the recommendations of the suppliers.

The pBR322 and pUC type plasmids and the phages of the M13 series are of commercial origin (Bethesda Research Laboratories).

For the ligations, the DNA fragments are separated according to their size by electrophoresis on agarose or acrylamide gels, extracted with phenol or with a phenol/chloroform mixture, precipitated with ethanol and then incubated in the presence of phage T4 DNA ligase (Biolabs) according to the recommendations of the manufacturer.

The filling of the protruding 5' ends is carried out by the Klenow fragment of DNA polymerase I of *E. coli* (Biolabs) according to the specifications of the supplier. The destruction of the protruding 3' ends is carried out in the presence of phage T4 DNA polymerase (Biolabs) used according to the recommendations of the manufacturer. The destruction of the protruding 5' ends is carried out by a controlled treatment with S1 nuclease.

Site-directed mutagenesis in vitro with synthetic oligodeoxynucleotides is carried out according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] is carried out using a "DNA thermal cycler" (Perkin Elmer Cetus) according to the specifications of the manufacturer.

The verification of the nucleotide sequences is carried out by the method developed by Sanger et al. [Proc. Natl. Acad. Sci. U.S.A., 74 (1977) 5463–5467] using the kit distributed by Amersham.

The transformations of *K. lactis* with DNA from the plasmids for expression of the proteins of the present invention are carried out by any technique known to persons skilled in the art, and of which an example is given in the text.

Except where otherwise stated, the bacterial strains used are *E. coli* MC1060 (lacIPOZYA, X74, galU, galK, strA$^r$), or *E. coli* TG1 (lac, proA,B, supE, thi, hsdD5/FtraD36, proA$^+$B$^+$, lacI$^q$, lacZ, M15).

The yeast strains used belong to the budding yeasts and more particularly to yeasts of the genus Kluyveromyces. The *K. lactis* MW98-8C (a, uraA, arg, lys, K$^+$, pKD1$^o$) and *K. lactis* CBS 293.91 strain were particularly used; a sample of the MW98-8C strain was deposited on 16 Sep. 1988 at Centraalbureau voor Schimmelkulturen (CBS) at Baarn (the Netherlands) where it was registered under the number CBS 579.88.

A bacterial strain (*E. coli*) transformed with the plasmid pET-8c52K was deposited on 17 Apr. 1990 with the American Type Culture Collection under the number ATCC 68306.

The yeast strains transformed with the expression plasmids encoding the proteins of the present invention are cultured in erlenmeyers or in 21 pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLE 1

COUPLING AT THE C-TERMINUS OF HSA

The plasmid pYG404 is described in Patent Application EP 361 991. This plasmid contains a HindIII restriction fragment encoding the prepro-HSA gene preceded by the 21 nucleotides naturally present immediately upstream of the initiator ATG for translation of the PGK gene of *S. cerevisiae.* The nucleotide sequence of this restriction fragment is included in that of FIG. 2. The MstII site localized in the coding sequence, three residues from the codon specifying the end of translation is particularly useful as site for cloning a biologically active peptide which it is desired to couple in translational phase at the C-terminus of HSA. In a specific embodiment, it is useful to use peptides whose sequence is encoded by an MstII-HindIII restriction fragment of the type: 5'-CCTTAGGCTTA [3xN] $_p$ TAAGCTT-3' (SEQ ID NO:20), the sequence encoding the biologically active peptide (p residues) is $[3xN]_p$). The ligation of this fragment to the HindIII-MstII restriction fragment corresponding to the entire gene encoding HSA, with the exception of the three C-terminalmost amino acids (leucin-glycine-leucin residues) generates a HindIII restriction fragment containing a hybrid gene encoding a chimeric protein of the HSA-PEPTIDE type (FIG. 1, panel A), immediately preceded by the "prepro" export region of HSA. In another embodiment, the biologically active peptide may be present more than once in the chimera.

EXAMPLE 2

COUPLING AT THE N-TERMINUS OF HSA

Figure 1A:
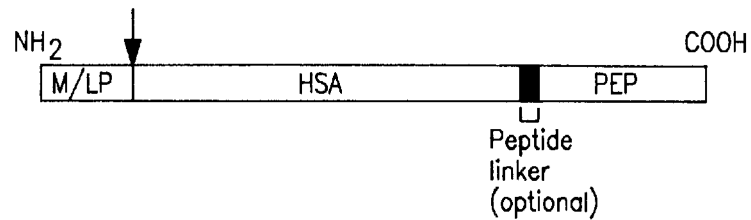
FIG. 1A is a schematic representation of the chimera of the HSA-PEPTIDE type.
Figure 1B:
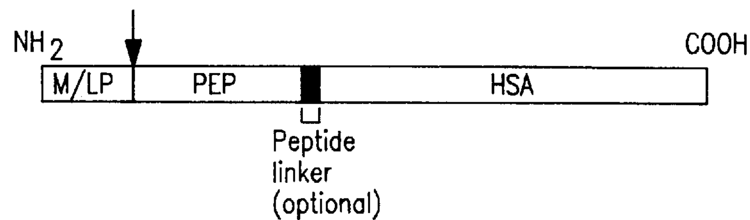
FIG. 1B is a schematic representation of a chimera of the PEPTIDE-HSA type.
Figure 1C:
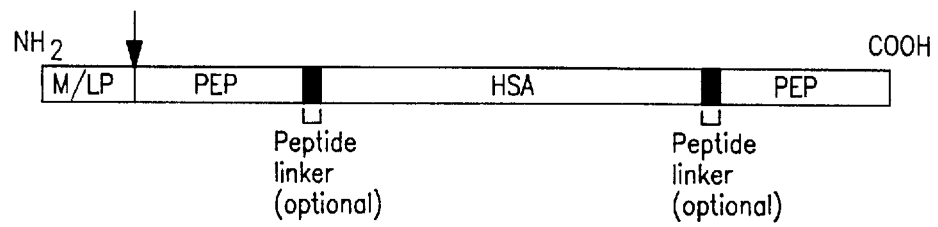
FIG. 1C is a schematic representation of a chimera of the PEPTIDE-HSA-PEPTIDE type. Abbreviations used: M/LP, translational initiator methionine residue, optionally followed by a signal sequence for secretion; HSA, mature albumin or one of its molecular variants; PEP, peptide of natural or artificial origin possessing a given therapeutic property. The PEP sequence may be present several times in the FIG. 1A, B or C molecules. The black arrow indicates the N-terminal end of the mature protein.

In a specific embodiment, the combined techniques of site-directed mutagenesis and PCR amplification make it possible to construct hybrid genes encoding a chimeric protein resulting from the translational coupling between a signal peptide (and for example the prepro region of HSA), a sequence including the biologically active peptide and the mature form of HSA or one of its molecular variants. These hybrid genes are preferably bordered in 5' of the translational initiator ATG and in 3' of the translational stop codon by HindIII restriction sites and encode chimeric proteins of the PEPTIDE-HSA type (FIG. 1, panel B). In a still more specific embodiment, the biologically active peptide may be present more than once in the chimera.

EXAMPLE 3

COUPLING AT THE N- AND C-TERMINUS OF HSA

The combined techniques of site-directed mutagenesis and PCR amplification described in Examples 1 and 2 make it possible to construct hybrid genes encoding a chimeric protein resulting from the translational coupling between the mature form of HSA, or one of its molecular variants, and a biologically active peptide coupled to the N- and C-terminal ends of HSA. These hybrid genes are preferably bordered in 5' of the translational initiator ATG and in 3' of the translational stop codon by HindIII restriction sites and encode chimeric proteins of the PEPTIDE-HSA-PEPTIDE type (FIG. 1, panel C), immediately preceded by the "prepro" export region of HSA. In a still more specific embodiment, the biologically active peptide may be present more than once in the chimera.

EXAMPLE 4

EXPRESSION PLASMIDS

Figure 3:
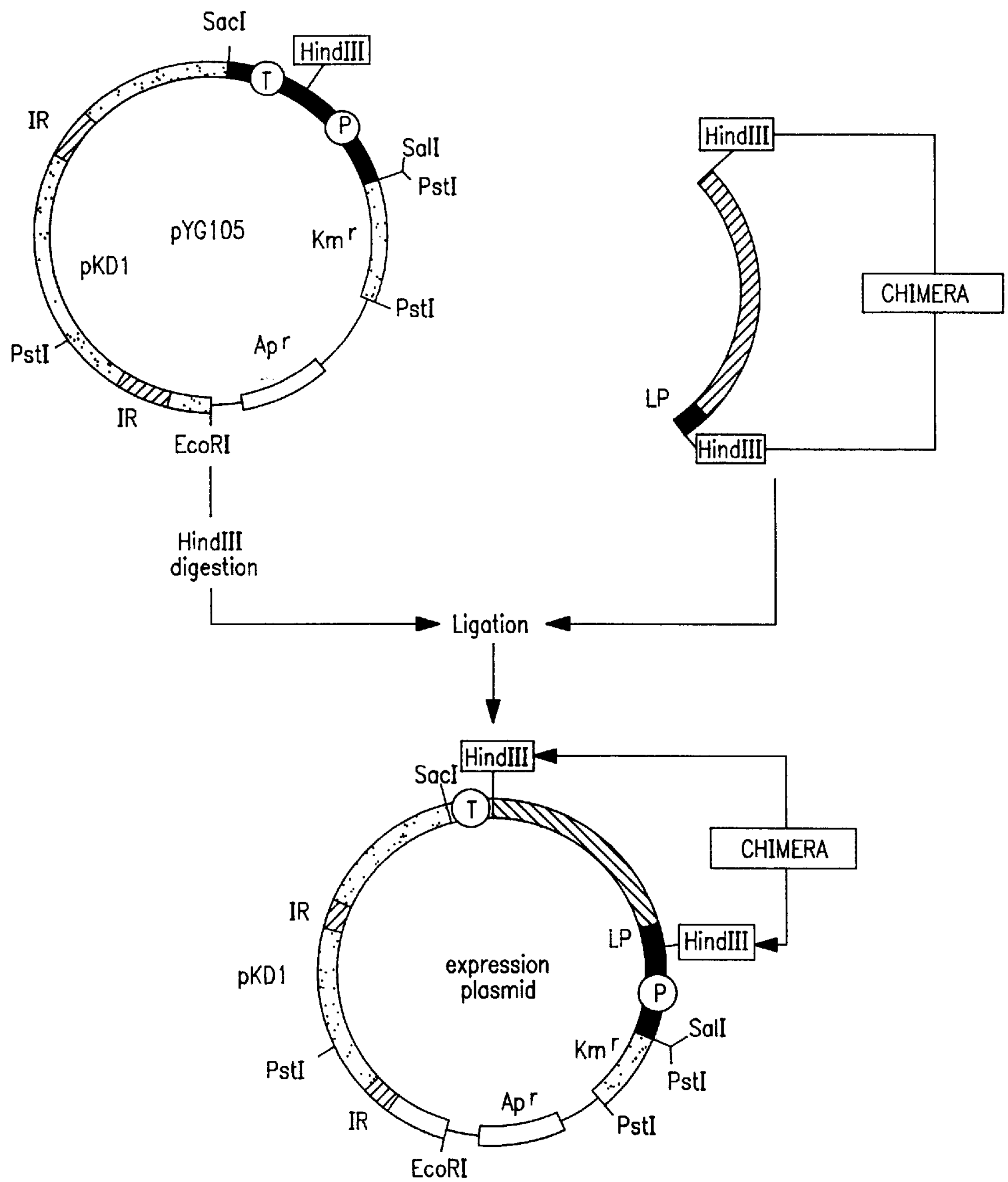
FIG. 3: Restriction map for the plasmid pYG105 and generic strategy for construction of the plasmids for expression of the chimeric proteins of the present invention. Abbreviations used: P, transcriptional promoter; T, transcriptional terminator; IR, inverted repeat sequences of the plasmid pKD1; LP, signal sequence for secretion; $Ap^r$ and $Km^r$ designate the genes for resistance to ampicillin (*E. coli*) and to G418 (yeasts), respectively.

The chimeric proteins of the preceding examples can be expressed in yeasts using functional, regulatable or constitutive promoters such as, for example, those present in the plasmids pYG105 (LAC4 promoter of *Kluyveromyces lactis*), pYG106 (PGK promoter of *Saccharomyces cerevisiae*), pYG536 (PHO5 promoter of *S. cerevisiae*), or hybrid promoters such as those described in Patent Application EP 361 991. The plasmids pYG105 and pYG106 are particularly useful here because they permit the expression of the genes encoded by the HindIII restriction fragments as described in the preceding examples and cloned into the HindIII site and in the productive orientation (defined as the orientation which places the "prepro" region of albumin proximally relative to the promoter for transcription), using promoters which are functional in *K. lactis,* regulatable (pYG105) or constitutive (pYG106). The plasmid pYG105 corresponds to the plasmid pKan707 described in Patent Application EP 361 991 in which the HindIII restriction site which is unique and localized in the gene for resistance to geneticin (G418) has been destroyed by site-directed mutagenesis while preserving an unchanged protein (oligodeoxynucleotide 5'-GAAATGCATAAGCTC TTGCCATTCTCACCG-3')(SEQ ID NO:21). The SalI-SacI fragment encoding the URA3 gene of the mutated plasmid was then replaced with a SalI-SacI restriction fragment containing an expression cassette consisting of the LAC4 promoter of *K. lactis* (in the form of a SalI-HindIII fragment) and the terminator of the PGK gene of *S. cerevisiae* (in the form of a HindIII-SacI fragment). The plasmid pYG105 is mitotically very stable in the Kluyveromyces yeasts and a restriction map thereof is given in FIG. 3. The plasmids pYG105 and pYG106 differ from each other only in the nature of the promoter for transcription encoded by the SalI-HindIII fragment.

EXAMPLE 5

TRANSFORMATION OF THE YEASTS

The transformation of the yeasts belonging to the genus Kluyveromyces, and in particular the strains MW98-8C and CBS 293.91 of *K. lactis* is carried out for example by the technique for treating whole cells with lithium acetate [Ito H. et al., J. Bacteriol. 153 (1983) 163–168], adapted as follows. The growth of the cells is carried out at 28° C. in 50 ml of YPD medium, with stirring and up to an optical density of 600 nm ($OD_{600}$) of between 0.6 and 0.8; the cells are harvested by centrifugation at low speed, washed in a sterile solution of TE (10 mM Tris HCl pH 7.4; 1 mM EDTA), resuspended in 3–4 ml of lithium acetate (0.1M in TE) in order to obtain a cellular density of about $2\times10^8$ cells/ml, and then incubated at 30° C. for 1 hour with moderate stirring. Aliquots of 0.1 ml of the resulting suspension of competent cells are incubated at 30° C. for 1 hour in the presence of DNA and at a final concentration of 35% polyethylene glycol ($PEG_{4000}$, Sigma). After a heat shock of 5 minutes at 42° C., the cells are washed twice, resuspended in 0.2 ml of sterile water and incubated for 16 hours at 28° C. in 2 ml of YPD medium in order to permit the phenotypic expression of the gene for resistance to G418 expressed under the control of the $P_{kl}$ promoter (cf. EP 361 991); 200 $\mu$l of the cellular suspension are then plated on selective YPD dishes (G418, 200 $\mu$g/ml). The dishes are incubated at 28° C. and the transformants appear after 2 to 3 days of cell growth.

EXAMPLE 6

SECRETION OF THE CHIMERAS

After selection on rich medium supplemented with G418, the recombinant clones are tested for their capacity to secrete the mature form of the chimeric proteins. Few clones, corresponding to the strain CBS 293.91 or MW98-8C transformed by the plasmids for expression of the chimeras between HSA and the biologically active part, are incubated in YPD or YPL medium at 28° C. The cellular supernatants are recovered by centrifugation when the cells reach the stationary growth phase, optionally concentrated 10 times by precipitation for 30 minutes at –20° C. in a final concentration of 60% ethanol, and then tested after electrophoresis on an 8.5% SDS-PAGE gel, either directly by staining the gel with coomassie blue, or after immunoblotting using primary antibodies directed against the biologically active part or a rabbit polyclonal serum directed against HSA. During the experiments for immunological detection, the nitrocellulose filter is first incubated in the presence of specific primary antibodies, washed several times, incubated in the presence of goat antibodies directed against the primary antibodies, and then incubated in the presence of an avidin-peroxidase complex using the "ABC kit" distributed by Vectastain (Biosys S. A., Compiègne, France). The immunological reaction is then revealed by the addition of 3,3'-diamino benzidine tetrahydrochloride (Prolabo) in the presence of hydrogen peroxide, according to the recommendations of the manufacturer.

EXAMPLE 7

CHIMERAS DERIVED FROM THE VON WILLEBRAND FACTOR

E.7.1. Fragments Antagonizing the Binding of vWF to the Platelets

E.7.1.1. Thr470-Val713 Residues of vWF

The plasmid pET-8c52K contains a fragment of the vWF cDNA encoding residues 445 to 733 of human vWF and therefore includes several crucial determinants of the interaction between vWF and the platelets on the one hand, and certain elements of the basal membrane and the sub-endothelial tissue on the other, and especially the peptides G10 and D5 which antagonize the interaction between vWF and GP1b [Mori H. et al., J. Biol. Chem. 263 (1988) 17901–17904]. This peptide sequence is identical to the corresponding sequence described by Titani et al. [Biochemistry 25, (1986) 3171–3184]. The amplification of these genetic determinants can be carried out using the plasmid pET-8c52K, for example by the PCR amplification technique, using as primer oligodeoxynucleotides encoding contiguous residues localized on either side of the sequence to be amplified. The amplified fragments are then cloned into vectors of the M13 type for their verification by sequencing using either the universal primers situated on either side of the multiple cloning site, or oligodeoxynucleotides specific for the amplified region of the vWF gene of which the sequence of several isomorphs is known [Sadler J. E. et al., Proc. Natl. Acad. Sci. 82 (1985) 6394–6398; Verweij C. L. et al., EMBO J. 5 (1986) 1839–1847; Shelton-Inloes B. B. et al., Biochemistry 25 (1986) 3164–3171; Bonthron D. et al., Nucleic Acids Res. 17 (1986) 7125–7127]. Thus, the PCR amplification of the plasmid pET-8c52K with the oligodeoxynucleotides 5'-CCCGGGATCCCTTAGGCTTAACCTGTGAAGC CTGC-3' (SEQ ID NO:22) (Sq1969, the MstII site is underlined) and 5'-CCCGGGATCCAAGCTTAGACTT GTGCCATGTCG-3' (SEQ ID NO:23) (Sq2029, the HindIII site is underlined) generates an MstII-HindIII restriction fragment including the Thr470 to Val713 residues of vWF (FIG. 4, panel E). The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation and into the HindIII site of the plasmid pYG105, which generates the expression plasmid pYG1248 (HSA-vWF470–713).

E.7.1.2. Molecular Variants:

In another embodiment, the binding site of vWF is a peptide including the Thr470 to Asp498 residues of the mature vWF. This sequence including the peptide G10 (Cys474-Pro488) described by Mori et al. [J. Biol. Chem. 263 (1988) 17901–17904] and capable of antagonizing the interaction of human vWF with the GP1b of the human platelets. The sequence corresponding to the peptide G10 is first included in an MstII-HindIII restriction fragment (FIG. 4, panel B), for example by PCR amplification of the plasmid pET-8c52K with the oligodeoxynucleotides Sq1969 and 5'-CCCGGGATCCAAGCTTAGTCCTCCACAT ACAG-3'(SEQ ID NO:24) (Sq1970, the HindIII site is underlined), which generates an MstII-HindIII restriction fragment including the peptide G10, and whose sequence is: 5'-CCTTAGGCTTAACCTGTGAAGCCTG-CCAGGAGC CGGGAGGCCTGGTGGTGCCTCCCACAGATGCCC CGGTGAGCCCC-ACCACTCTGTATGTGGAGGACT AAGCTT-3' (SEQ ID NO:25) (the sequence encoding the peptide G10 is in bold characters). The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation into the HindIII site of the plasmid pYG105, which generates the expression plasmid pYG1214.

In another embodiment, the site for binding of vWF to GP1b is directly designed with the aid of synthetic oligodeoxynucleotides, and for example the oligodeoxynucleotides 5'-TTAGGCCTCTGTGACCTTGCCCCTGA-AGCCCCTCCTCCTACTCTGCCCCCCTAAGCTTA-3' (SEQ ID NO:26) and 5'-GATCTAAG-CTTAGG GGGGCAGAGTAGGAGGAGGGGCT TCAGGGGCAAGGTCACAGAGGCC-3' (SEQ ID NO:27). These oligodeoxynucleotides form, by pairing, a MstII-BglII restriction fragment including the MstII-HindIII fragment (FIG. 4, panel C) corresponding to the peptide D5 defined by the Leu694 to Pro708 residues of vWF. The ligation of the MstII-HindIII fragment to the HindIII-MstII restriction fragment corresponding to the entire gene encoding HSA with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation into the HindIII site of the plasmid pYG105, which generates the expression plasmid pYG1206.

Useful variants of the plasmid pET-8c52K are deleted by site-directed mutagenesis between the peptides G10 and G5, for example sites for binding to collagen, and/or to heparin, and/or to botrocetin, and/or to sulphatides and/or to ristocetin. One example is the plasmid pMMB9 deleted by site-directed mutagenesis between the residues Cys509 and Ile662. The PCR amplification of this plasmid with the oligodeoxynucleotides Sq1969 and Sq2029 generates an MstII-HindIII restriction fragment (FIG. 4, panel D) including the Thr470 to Tyr508 and Arg663 to Val713 residues and in particular the peptides G10 and D5 of vWF and deleted in particular of its site for binding to collagen localized between the residues Glu542 and Met622 [Roth G. J. et al., Biochemistry 25 (1986) 8357–8361]. The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "pre-pro" export region of HSA. This restriction fragment is cloned in the productive orientation into the HindIII site of the plasmid pYG105, which generates the expression plasmid pYG1223.

In other embodiments, the use of combined techniques of site-directed mutagenesis and PCR amplification makes it possible to generate at will variants of the MstII-HindIII restriction fragment of panel A of FIG. 4 but deleted of one or more sites for binding to sulphatides and/or to botrocetin and/or to heparin and/or to collagen, and/or substituted by any residue involved in the vWF-associated emergence of IIB type pathologies.

In other useful variants of the plasmid pET-8c52K, mutations are introduced, for example by site-directed mutagenesis, in order to replace or suppress all or part of the set of cysteines present at positions 471, 474, 509 and 695 of the human vWF. Specific examples are the plasmids p5E and p7E in which the cysteins present at positions 471 and 474, on the one hand, and at positions 471, 474, 509 and 695, on the other hand, have been respectively replaced by glycine residues. The PCR amplification of these plasmids with the oligodeoxynucleotides Sq2149 (5'-CCCGGGATC CCTTAGGCTTAACCGGTGAAGCCGGC-3' (SEQ ID NO:28), the MstII site is underlined) and Sq2029 makes it possible to generate MstII-HindIII restriction fragments including the Thr470 to Val713 residues of the natural vWF with the exception that at least the cystein residues at positions 471 and 474 were mutated to glycine residues. The ligation of these fragments to the HindIII-MstII restriction fragment corresponding to the entire gene encoding HSA with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. These restriction fragments are cloned in the productive orientation into the HindIII site of the plasmid pYG105, which generates the expression plasmids pYG1283 (chimera HSA-vWF470–713, C471G, C474G) and pYG1279 (chimera HSA-vWF470–713, C471G, C474G, C509G, C695G).

Other particularly useful mutations affect at least one residue involved in vWF-associated type IIB pathologies (increase in the intrinsic affinity of vWF for GP1b), such as the residues Arg543, Arg545, Trp550, Val551, Val553, Pro574 or Arg578 for example. The genetic recombination techniques in vitro also make it possible to introduce at will one or more additional residues into the sequence of vWF and for example a supernumerary methionine between positions Asp539 and Glu542.

E.7.2. Fragments Antagonizing the Binding of vWF to the Sub-Endothelium

In a specific embodiment, the sites for binding of vWF to the components of the sub-endothelial tissue, and for example collagen, are generated by PCR amplification of the plasmid pET-8c52K, for example with the oligodeoxynucleotides Sq2258 (5'-GGATCCTTAGGGCTGTGCAGCAG GCTACTGGACCTGGTC-3' (SEQ ID NO:29), the MstII site is underlined) and Sq2259 (5'-GAATTC AAGCTTAACAGAGGTAGCTAA-CGATCTCGTCCC-3' (SEQ ID NO:30), the HindIII site is underlined), which generates an MstII-HindIII restriction fragment encoding the Cys509 to Cys695 residues of the natural vWF. Deletion molecular variants or modified variants are also generated which contain any desired combination between the sites for binding of vWF to the sulphatides and/or to botrocetin and/or to heparin and/or to collagen and/or any residue responsible for a modification of the affinity of vWF for GP1b (vWF-associated type II pathologies). In another embodiment, the domain capable of binding to collagen may also come from the vWF fragment which is between the residues 911 and 1114 and described by Pareti et al. [J. Biol. Chem. (1987) 262: 13835–13841]. The ligation of these fragments to the HindIII-MstII restriction fragment corresponding to the entire gene encoding HSA with the exception of the three C-terminalmost amino acids (cf. FIG. 2) generates HindIII restriction fragments containing a hybrid gene encoding a chimeric protein of the HSA-PEPTIDE type (FIG. 1, panel A), immediately preceded by the "pre-pro" export region of HSA. These restriction fragments are cloned in the productive orientation into the HindIII site of the plasmid pYG105, which generates the corresponding expression plasmids, and for example the plasmid pYG1277 (HSA-vWF509–695).

Figure 5A:
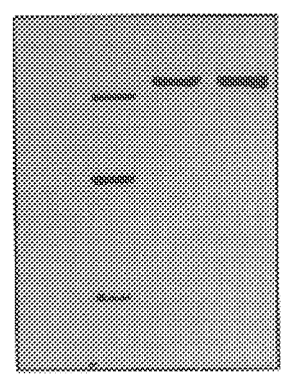
FIGS. 5A, 5B, and 5C collectively show the characterization of the material secreted after 4 days of culture (erlenmeyers) of the strain CBS 293.91 transformed with the plasmids pYG1248 (plasmid for expression of a chimera of the HSA-vWF Thr470→Val713) and pKan707 (control plasmid). In this experiment, the polypeptides for FIGS. 5A, 5B, and 5C were run on the same gel (8.5% SDS-PAGE) and then treated separately.
Figure 5B:
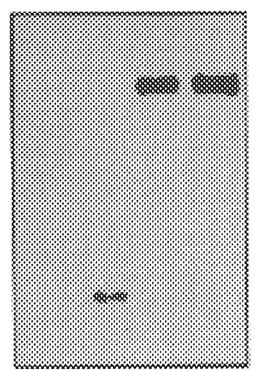
Figure 5C:
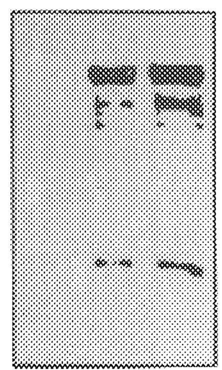

E.7.3. Purification and Molecular Characterization of the Chimeras Between HSA and vWF The chimeras present in the culture supernatants corresponding to the CBS 293.91 strain transformed, for example with the expression plasmids according to Examples E.7.1. and E.7.2., are characterized in a first instance by means of antibodies specific for the HSA part and for the vWF part. The results of FIGS. 5 to 7 demonstrate that the yeast *K. lactis* is capable of secreting chimeric proteins between HSA and a fragment of vWF, and that these chimeras are immunologically reactive. It may also be desirable to purify some of these chimeras. The culture is then centrifuged (10,000 g, 30 min), the supernatant is passed through a 0.22 mm filter (Millipore) and then concentrated by ultrafiltration (Amicon) using a membrane whose discrimination threshold is situated at 30 kDa. The concentrate obtained is then dialysed against a Tris-HCl solution (50 mM pH 8) and then purified on a column. For example, the concentrate corresponding to the culture supernatant of the CBS 293.91 strain transformed with the plasmid pYG1206 is purified by affinity chromatography on Blue-Trisacryl (IBF). A purification by ion-exchange chromatography can also be used. For example, in the case of the chimera HSA-vWF470–713, the concentrate obtained after ultrafiltration is dialysed against a Tris-HCl solution (50 mM pH 8), and then loaded in 20 ml fractions onto a cation-exchange column (5 ml) (S Fast Flow, Pharmacia) equilibrated in the same buffer. The column is then washed several times with the Tris-HCl solution (50 mM pH 8) and the chimeric protein is then eluted from the column by an NaCl gradient (0 to 1M). The fractions containing the chimeric protein are then pooled and dialysed against a 50 mM Tris-HCl solution (pH 8) and then reloaded onto the S Fast Flow column. After elution of the column, the fractions containing the protein are pooled, dialysed against water and freeze-dried before characterization: for example, sequencing (Applied Biosystem) of the protein [HSA-vWF470–704 C471G, C474G] secreted by the yeast CBS 293.91 gives the N-terminal sequence expected for HSA (Asp-Ala-His . . . ), demonstrating a correct maturation of the chimera immediately at the C-terminus of the doublet of residues Arg-Arg of the "pro" region of HSA (FIG. 2). The essentially monomeric character of the chimeric proteins between HSA and vWF is also confirmed by their elution profile on a TSK 3000 column [Toyo Soda Company, equilibrated with a cacodylate solution (pH 7) containing 0.2M $Na_2SO_4$]: for example the chimera [HSA-vWF 470–704 C471G, C474G] behaves under the conditions like a protein with an apparent molecular weight of 95 kDa, demonstrating its monomeric character.

EXAMPLE 8

CHIMERAS DERIVED FROM UROKINASE

E.8.1. Constructs

A fragment corresponding to the amino-terminal fragment of urokinase (ATF: EGF-like domain+ringle domain) can be obtained from the corresponding messenger RNA of cells of certain human carcinoma, for example using the RT-PCR kit distributed by Pharmacia. An MstII-HindIII restriction fragment including the ATF of human urokinase is given in FIG. 8. The ligation of the HindIII-MstII fragment of the plasmid pYG404 to this MstII-HindIII fragment makes it possible to generate the HindIII fragment of the plasmid pYG1341 which encodes a chimeric protein in which the HSA molecule is genetically coupled to the ATF (HSA-UK1→135). Likewise, the plasmid pYG1340 contains a HindIII fragment encoding a chimera composed of HSA immediately followed by the first 46 residues of human urokinase (HSA-UK1→46, cf. FIG. 8). The cloning in the productive orientation, of the HindIII restriction fragment of the plasmid pYG1340 (HSA-UK1→46) into the HindIII site of the plasmids pYG105 (LAC4) and pYG106 (PGK) generates the expression plasmids pYG1343 and pYG1342 respectively. Likewise, the cloning, in the productive orientation, of the HindIII restriction fragment of the plasmid pYG1341 (HSA-UK1→135) into the HindIII site of the plasmids pYG105 (LAC4) and pYG106 (PGK) generates the expression plasmids pYG1345 and pYG1344 respectively.

E.8.2. Secretion of the Hybrids

Figure 9:
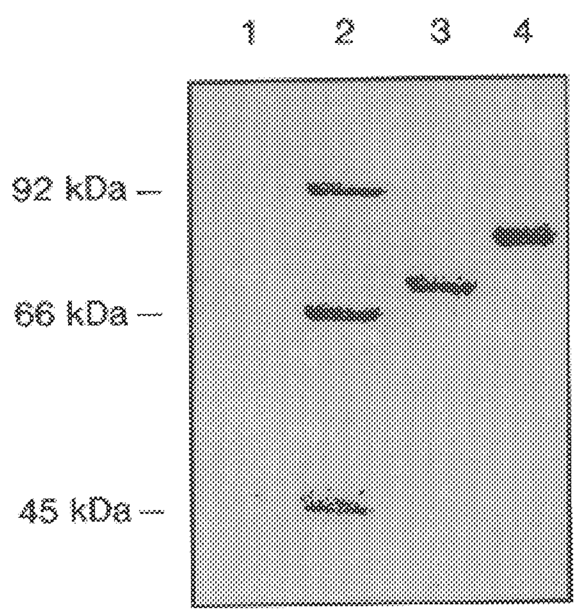
FIG. 9: Secretion of the HSA-UK1–46 and HSA-UK1–135 chimeras by the strain CBS 293.91 respectively transformed with the plasmids pYG1343 (HSA-UK1–46) and pYG1345 (HSA-UK1–135), after 4 days of growth (YPL+G418 medium). The deposits (equivalent to 50 μl of culture) are run on an 8.5% PAGE-SDS gel and stained with coomassie blue: supernatant from a clone transformed with the plasmids pKan707 (lane 1), pYG1343 (lane 3) or pYG1345 (lane 4); molecular weight standard (lane 2).

After selection on rich medium supplemented with G418, the recombinant clones are tested for their capacity to secrete the mature form of the chimeric proteins HSA-UK. A few clones corresponding to the strain *K. lactis* CBS 293.91, which is transformed with the expression plasmids according to Example E.9.1., are incubated in selective complete liquid medium at 28° C. The cellular supernatants are then tested after electrophoresis on an 8.5% acrylamide gel, either directly by staining of the gel with coomassie blue, or after immunoblotting using as primary antibodies a rabbit polyclonal serum directed against human albumin or against human urokinase. The results of FIG. 9 demonstrate that the hybrid proteins HSA-UK1→46 and HSA-UK1→135 are particularly well secreted by the yeast Kluyveromyces.

E.8.3 Purification of the Chimeras Between HSA and Urokinase

After centrifugation of a culture of the CBS 293.91 strain transformed with the expression plasmids according to Example E.8.1., the culture supernatant is passed through a 0.22 mm filter (Millipore) and then concentrated by ultrafiltration (Amicon) using a membrane whose discrimination threshold is situated at 30 kDa. The concentrate obtained is then adjusted to 50 mM Tris-HCl starting with a stock solution of 1M Tris-HCl (pH 7), and then loaded in 20 ml fractions onto an anion-exchange column (3 ml) (D-Zephyr, Sepracor) equilibrated in the same buffer. The chimeric protein (HSA-UK1→46 or HSA-UK1→135) is then eluted from the column by a gradient (0 to 1M) of NaCl. The fractions containing the chimeric protein are then pooled and dialysed against a 50 mM Tris-HCl solution (pH 6) and reloaded onto a D-Zephyr column equilibrated in the same buffer. After elution of the column, the fractions containing the protein are pooled, dialysed against water and freeze-dried before characterization of their biological activity and especially with respect to their ability to displace urokinase from its cellular receptor.

EXAMPLE 9

CHIMERAS DERIVED FROM G-CSF

E.9.1. Constructs

E.9.1.1. Coupling at the C-terminus of HSA.

An MstII-HindIII restriction fragment including the mature form of human G-CSF is generated, for example according to the following strategy: a KpnI-HindIII restriction fragment is first obtained by the enzymatic PCR amplification technique using the oligodeoxynucleotides Sq2291 (5'-CAAGGATCC-AAGCTTCAGGGCTGCGCAAGGTG GCGTAG-3' (SEQ ID NO:31), the HindIII site is underlined) and Sq2292 (5'-CGGGGTACCTTAGGC TTAACCCCCCTG-GGCCCTGCCAGC-3' (SEQ ID NO:32), the KpnI site is underlined) as primer on the plasmid BBG13 serving as template. The plasmid BBG13 contains the gene encoding the B form (174 amino acids) of mature human G-CSF, which is obtained from British Biotechnology Limited, Oxford, England. The enzymatic amplification product of about 550 nucleotides is then digested with the restriction enzymes KpnI and HindIII and cloned into the vector pUC19 cut with the same enzymes, which generates the recombinant plasmid pYG1255. This plasmid is the source of an MstII-HindIII restriction fragment which makes it possible to fuse G-CSF immediately downstream of HSA (chimera HSA-G.CSF) and whose nucleotide sequence is given in FIG. 10.

It may also be desirable to insert a peptide linker between the HSA part and G-CSF, for example in order to permit a better functional presentation of the transducing part. An MstII-HindIII restriction fragment is for example generated by substitution of the MstII-ApaI fragment of the plasmid pYG1255 by the oligodeoxynucleotides Sq2742 (5'-TTAGGCTTAGGTGGTGGCGGT-ACCCCCCTGGGCC -3' (SEQ ID NO:33), the codons encoding the glycine residues of this particular linker are underlined) and Sq2741 (5'-CAGGGGGGTACCGCCACCACCTAAGCC-3') (SEQ ID NO:34) which form, by pairing, an MstII-ApaI fragment. The plasmid thus generated therefore contains an MstII-HindIII restriction fragment whose sequence is identical to that of FIG. 10 with the exception of the MstII-ApaI fragment.

The ligation of the HindIII-MstII fragment of the plasmid pYG404 to the MstII-HindIII fragment of the plasmid pYG1255 makes it possible to generate the HindIII fragment of the plasmid pYG1259 which encodes a chimeric protein in which the B form of the mature G-CSF is positioned by genetic coupling in translational phase at the C-terminus of the HSA molecule (HSA-G.CSF).

An identical HindIII restriction fragment, with the exception of the MstII-ApaI fragment, may also be easily generated and which encodes a chimeric protein in which the B form of the mature G-CSF is positioned by genetic coupling in translational phase at the C-terminus of the HSA molecule and a specific peptide linker. For example, this linker consists of 4 glycine residues in the HindIII fragment of the plasmid pYG1336 (chimera HSA-$Gly_4$-G.CSF).

The HindIII restriction fragment of the plasmid pYG1259 is cloned in the productive orientation and into the HindIII restriction site of the expression plasmid pYG105, which generates the expression plasmid pYG1266 (HSA-G.CSF). In another exemplification, the cloning of the HindIII restriction fragment of the plasmid pYG1259 in the productive orientation and into the HindIII site of the plasmid pYG106 generates the plasmid pYG1267. The plasmids pYG1266 and pYG1267 are mutually isogenic with the exception of the SalI-HindIII restriction fragment encoding the LAC4 promoter of *K. lactis* (plasmid pYG1266) or the PGK promoter of *S. cerevisiae* (plasmid pYG1267).

In another exemplification, the cloning in the productive orientation of the HindIII restriction fragment of the plasmid pYG1336 (chimera HSA-$Gly_4$-G.CSF) into the HindIII site of the plasmids pYG105 (LAC4) and pYG106 (PGK) generates the expression plasmids pYG1351 and pYG1352 respectively.

E.9.1.2. Coupling at the N-terminus of HSA

In a specific embodiment, the combined techniques of site-directed mutagenesis and PCR amplification make it possible to construct hybrid genes encoding a chimeric protein resulting from the translational coupling between a signal peptide (and for example the prepro region of HSA), a sequence including a gene having a G-CSF activity, and the mature form of HSA or one of its molecular variants (cf. chimera of panel B, FIG. 1). These hybrid genes are preferably bordered in 5' of the translational initiator ATG and in 3' of the translational stop codon by HindIII restriction sites. For example the oligodeoxynucleotide Sq2369 (5'-GTTCTACGCCACCTTGCGCAG-CCC GGTGGAGGCGGTGATGCACACAAGAGTGAGGTT GCTCATCGG-3' (SEQ ID NO:35) the residues underlined (optional) correspond in this particular chimera to a peptide linker composed of 4 glycine residues) makes it possible, by site-directed mutagenesis, to put in translational phase the mature form of the human G-CSF of the plasmid BBG13 immediately upstream of the mature form of HSA, which generates the intermediate plasmid A. Likewise, the use of the oligodeoxynucleotide Sq2338 [5'-CAGGGAGCTGGCAGGGCCCAGGGGGGTTCGACG AAACACACCCCTGGAATAAGCCGAGCT-3' (SEQ ID NO:36) (non-coding strand), the nucleotides complementary to the nucleotides encoding the first N-terminal residues of the mature form of the human G-CSF are underlined] makes it possible, by site-directed mutagenesis, to couple in translational reading phase the prepro region of HSA immediately upstream of the mature form of the human G-CSF, which generates the intermediate plasmid B. A HindIII fragment encoding a chimeric protein of the PEPTIDE-HSA type (cf. FIG. 1, panel B) is then generated by combining the HindIII-SstI fragment of the plasmid B (joining prepro region of HSA+N-terminal fragment of the mature G-CSF) with the SstI-HindIII fragment of the plasmid A [joining mature G-CSF-$(glycine)_{x4}$- mature HSA]. The plasmid pYG1301 contains this specific HindIII restriction fragment encoding the chimera G.CSF-$Gly_4$-HSA fused immediately downstream of the prepro region of HSA (FIG. 11). The cloning of this HindIII restriction fragment in the productive orientation and into the HindIII site of the plasmids pYG105 (LAC4) and pYG106 (PGK) generates the expression plasmids pYG1302 and pYG1303 respectively.

E.9.2. Secretion of the Hybrids.

Figures 12A, 12B, 12C:
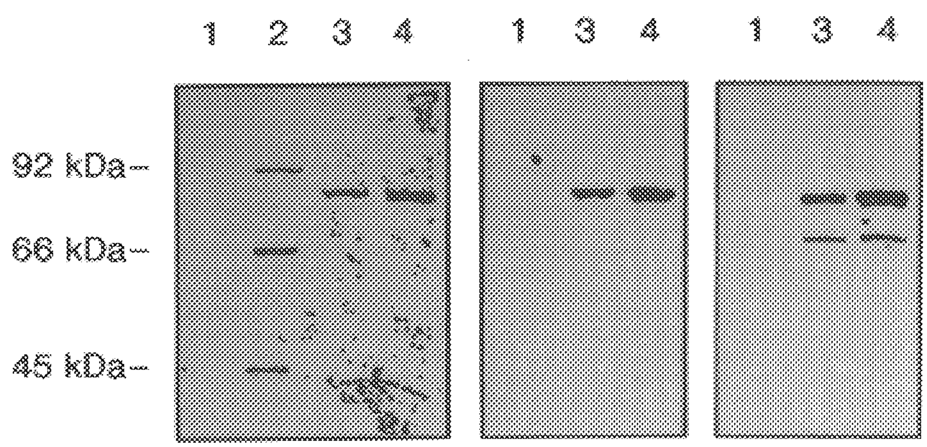
FIGS. 12A, 12B, and 12C collectively show the characterization of the material secreted after 4 days of culture (erlenmeyers) of the strain CBS 293.91 transformed with the plasmids pYG1266 (plasmid for expression of a chimera of the HSA-G.CSF type) and pKan707 (control plasmid). In this experiment, the polypeptides for FIGS. 12A, 12B, 12C were run on the same gel (8.5% SDS-PAGE) and then treated separately.
Figure 13A:
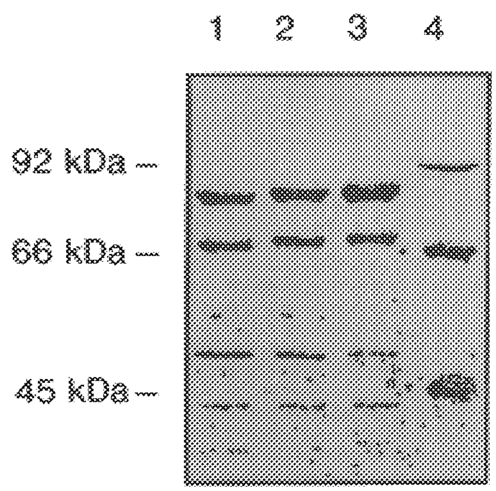
FIGS. 13A and B collectively show the characterization of the material secreted after 4 days of culture (erlenmeyers in YPD medium) of the strain CBS 293.91 transformed with the plasmids pYG1267 (chimera HSA-G.CSF), pYG1303 (chimera G.CSF-$Gly_4$-HSA) and pYG1352 (chimera HSA-$Gly_4$-G.CSF) after running on an 8.5% SDS-PAGE gel.
Figure 13B:
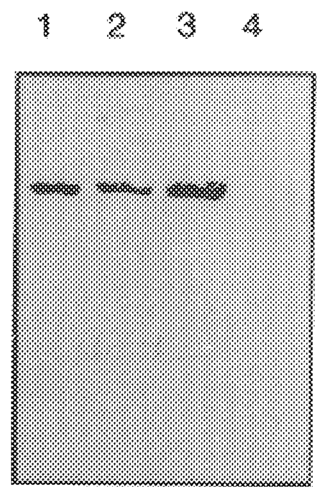

After selection on rich medium supplemented with G418, the recombinant clones are tested for their capacity to secrete the mature form of the chimeric proteins between HSA and G-CSF. A few clones corresponding to the strain *K. lactis* CBS 293.91 transformed with the plasmids pYG1266 or pYG1267 (HSA-G.CSF), pYG1302 or pYG1303 (G.CSF-$Gly_4$-HSA) or alternatively pYG1351 or pYG1352 (HSA-$Gly_4$-G.CSF) are incubated in selective complete liquid medium at 28° C. The cellular supernatants are then tested after electrophoresis on an 8.5% acrylamide gel, either directly by staining the gel with coomassie blue, or after immunoblotting using as primary antibodies rabbit polyclonal antibodies directed against the human G-CSF or a rabbit polyclonal serum directed against human albumin. The results of FIG. 12 demonstrate that the hybrid protein HSA-G.CSF is recognized both by antibodies directed against human albumin (panel C) and human G-CSF (panel B). The results of FIG. 13 indicate that the chimera HSA-$Gly_4$-G.CSF (lane 3) is particularly well secreted by the yeast Kluyveromyces, possibly because of the fact that the presence of the peptide linker between the HSA part and the G-CSF part is more favourable to an independent folding of these 2 parts during the transit of the chimera in the secretory pathway. Furthermore, the N-terminal fusion (G.CSF-$Gly_4$-HSA) is also secreted by the yeast Kluyveromyces (FIG. 13, lane 1).

E.9.3. Purification and Molecular Characterization of the Chimeras Between HSA and G-CSF.

After centrifugation of a culture of the CBS 293.91 strain transformed with the expression plasmids according to Example E.9.1., the culture supernatant is passed through a 0.22 mm filter (Millipore) and then concentrated by ultrafiltration (Amicon) using a membrane whose discrimination threshold is situated at 30 kDa. The concentrate obtained is then adjusted to 50 mM Tris-HCl from a 1M stock solution of Tris-HCl (pH 6), and then loaded in 20 ml fractions onto an ion-exchange column (5 ml) (Q Fast Flow, Pharmacia) equilibrated in the same buffer. The chimeric protein is then eluted from the column by a gradient (0 to 1M) of NaCl. The fractions containing the chimeric protein are then pooled and dialysed against a 50 mM Tris-HCl solution (pH 6) and reloaded onto a Q Fast Flow column (1 ml) equilibrated in the same buffer. After elution of the column, the fractions containing the protein are pooled, dialysed against water and freeze-dried before characterization: for example, the sequencing (Applied Biosystem) of the protein HSA-G.CSF secreted by the yeast CBS 293.91 gives the N-terminal sequence expected for HSA (Asp-Ala-His . . . ), demonstrating a correct maturation of the chimera immediately at the C-terminus of the doublet of residues Arg-Arg of the "pro" region of HSA (FIG. 2).

EXAMPLE 10

CHIMERAS DERIVED FROM AN IMMUNOGLOBULIN

E.10.1. Constructs

An Fv' fragment can be constructed by genetic engineering techniques, and which encodes the variable fragments of the heavy and light chains of an immunoglobulin (Ig), linked to each other by a linker peptide [Bird et al., Science (1988) 242: 423; Huston et al., (1988) Proc. Natl. Acad. Sci. 85: 5879]. Schematically, the variable regions (about 120 residues) of the heavy and light chains of a given Ig are cloned from the messenger RNA of the corresponding hybridoma, for example using the RT-PCR kit distributed by Pharmacia (Mouse ScFv module). In a second stage, the variable regions are genetically coupled by genetic engineering via a synthetic linkage peptide and for example the linker $(GGGGS)_{x3}$. An MstII-HindIII restriction fragment including the Fv' fragment of an immunoglobulin secreted by a murine hybridoma is given in FIG. 14. The ligation of the HindIII-MstII fragment of the plasmid pYG404 to this MstII-HindIII fragment makes it possible to generate the HindIII fragment of the plasmid pYG1382 which encodes a chimeric protein in which the HSA molecule is genetically coupled to the Fv' fragment of FIG. 14 (chimera HSA-Fv'). The cloning in the productive orientation of the HindIII restriction fragment of the plasmid pYG1382 into the HindIII site of the plasmids pYG105 (LAC4) and pYG106 (PGK) generates the expression plasmids pYG1383 and pYG1384 respectively.

E.10.2. Secretion of the Hybrids

After selection on rich medium supplemented with G418, the recombinant clones are tested for their capacity to secrete the mature form of the chimeric protein HSA-Fv'. A few clones corresponding to the strain *K. lactis* CBS 293.91 transformed with the plasmids pYG1383 or pYG1384 (HSA-Fv') are incubated in selective complete liquid medium at 28° C. The cellular supernatants are then tested after electrophoresis on an 8.5% acrylamide gel, either directly by staining of the gel with coomassie blue, or after immunoblotting using as primary antibodies a rabbit polyclonal serum directed against human albumin, or directly incubated with biotinylated antibodies directed against the immunoglobulins of murine origin. The results of FIG. 15 demonstrate that the hybrid protein HSA-Fv' is recognized both by antibodies directed against human albumin (panel C) and reacts with biotinylated goat antibodies which are immunologically reactive towards mouse immunoglobulins (panel B).

EXAMPLE 11

BIOLOGICAL ACTIVITY OF THE CHIMERAS

E.11.1. Biological Activity In Vitro.

E.11.1.1. Chimeras Between HSA and vWF.

Figure 6A:
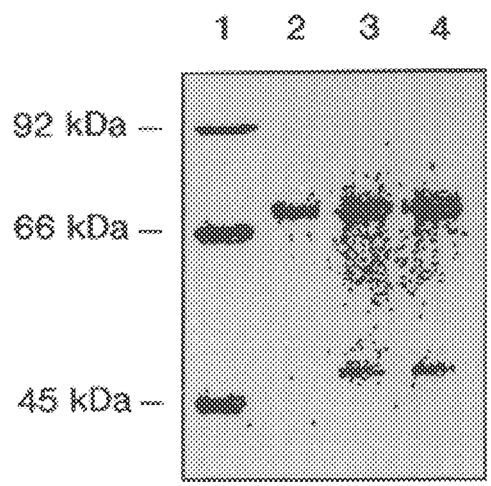
FIGS. 6A and 6B show the kinetic analysis of secretion of a chimera of the invention by the strain CBS 293.91 transformed with the plasmid pYG1206 (HSA-vWF Leu694-Pro708).
Figure 6B:
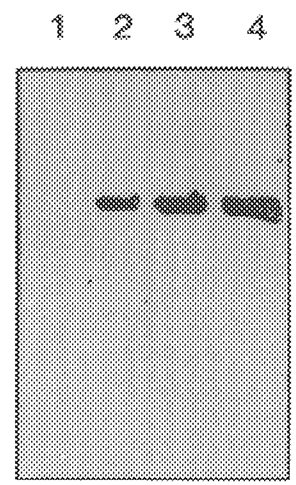
Figure 7:
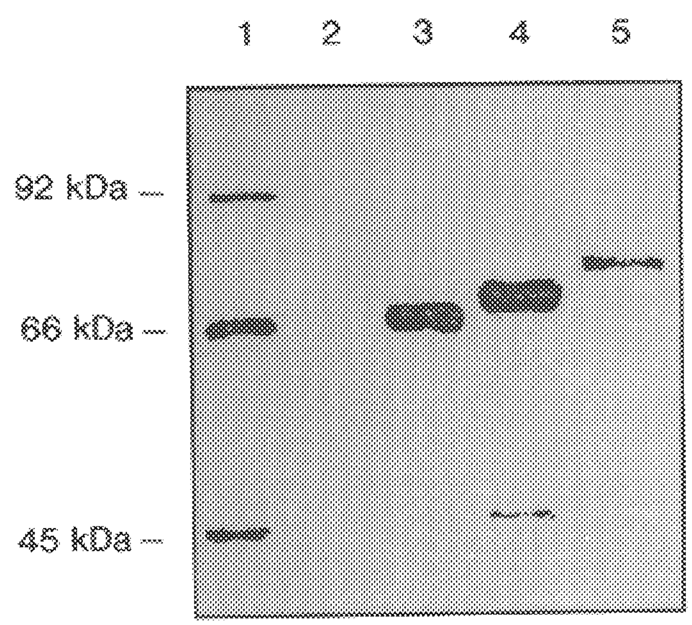
FIG. 7: Characterization of the material secreted by *K. lactis* transformed with the plasmids pKan707 (control plasmid, lane 2), pYG1206 (lane 3), pYG1214 (lane 4) and pYG1223 (lane 5); molecular weight standard (lane 1). The deposits correspond to 50 μl of supernatant from a stationary culture after growing in YPD medium, running on an 8.5% acrylamide gel and staining with coomassie blue.

The antagonistic activity of the products is determined by measuring the dose-dependent inhibition of the agglutination of human platelets fixed with paraformaldehyde according to the method described by Prior et al. [Bio/Technology (1992) 10: 66]. The measurements are carried out in an aggregameter (PAP-4, Bio Data, Horsham, Pa., U.S.A.) which records the variations over time of the optical transmission, with stirring, at 37° C. in the presence of vWF, of botrocetin (8.2 mg/ml) and of the test product at various dilutions (concentrations). For each measurement, 400 ml ($8\times10^7$ platelets) of a suspension of human platelets stabilized with paraformaldehyde (0.5%, and then resuspended in [NaCl (137 mM); $MgCl_2$ (1 mM); $NaH_2PO_4$ (0.36 mM); $NaHCO_3$ (10 mM); KCl (2.7 mM); glucose (5.6 mM); HSA (3.5 mg/ml); HEPES buffer (10 mM, pH 7.35)] are preincubated at 37° C. in the cylindrical tank (8.75×50 mm, Wellcome Distriwell, 159 rue Nationale, Paris) of the aggregameter for 4 min and are then supplemented with 30 ml of the solution of the test product at various dilutions in apyrogenic formulation vehicle [mannitol (50 g/l); citric acid (192 mg/l); L-lysine monohydrochloride (182.6 mg/l); NaCl (88 mg/l); pH adjusted to 3.5 by addition of NaOH (1M)], or formulation vehicle alone (control assay). The resulting suspension is then incubated for 1 min at 37° C. and 12.5 ml of human vWF [American Bioproducts, Parsippany, N.J., U.S.A.; 11% von Willebrand activity measured according to the recommendations for the use of PAP-4 (Platelet Aggregation Profiler®) with the aid of platelets fixed with formaldehyde ($2\times10^5$ platelets/ml), human plasma containing 0 to 100% vWF and ristocetin (10 mg/ml, cf. p. 36–45: vW Program™] are added and incubated at 37° C. for 1 min before adding 12.5 ml of botrocetin solution [purified from freeze-dried venom of *Bothrops jararaca* (Sigma) according to the procedure described by Sugimoto et al., Biochemistry (1991) 266: 18172]. The recording of the reading of the transmission as a function of time is then carried out for 2 min with stirring by means of a magnetic bar (Wellcome Distriwell) placed in the tank and with a magnetic stirring of 1,100 rpm provided by the aggregameter. The mean variation of the optical transmission ($n^3 5$ for each dilution) over time is therefore a measurement of the platelet agglutination due to the presence of vWF and botrocetin, in the absence or in the presence of variable concentrations of the test product. From such recordings, the % inhibition of the platelet agglutination due to each concentration of product is then determined and the straight line giving the % inhibition as a function of the reciprocal of the product dilution in log-log scale is plotted. The IC50 (or concentration of product causing 50% inhibition of the agglutination) is then determined on this straight line. The table of FIG. 6 compares the IC50 values of some of the HSA-vWF chimeras of the present invention and demonstrates that some of them are better antagonists of platelet agglutination than the product RG12986 described by Prior et al. [Bio/Technology (1992) 10: 66] and included in the assays as standard value. Identical tests for the inhibition of the agglutination of human platelets in the presence of vWF of pig plasma (Sigma) makes it possible, furthermore, to demonstrate that some of the hybrids of the present invention, and especially some type IIB variants, are very good antagonists of platelet agglutination in the absence of botrocetin-type cofactors. The botrocetin-independent antagonism of these specific chimeras can also be demonstrated according to the procedure initially described by Ware et al. [Proc. Natl. Acad. Sci. (1991) 88: 2946] by displacing the monoclonal antibody $^{125}$I-LJ-IB1 (10 mg/ml), a competitive inhibitor of the binding of vWF to the platelet GPIb [Handa M. et al., (1986) J. Biol. Chem. 261: 12579] after 30 min of incubation at 22° C. in the presence of fresh platelets ($10^8$ platelets/ml).

E.11.1.2. Chimeras between HSA and G-CSF

The purified chimeras are tested for their capacity to permit the in vitro proliferation of the IL3-dependant murine line NFS60, by measuring the incorporation of tritiated thymidine essentially according to the procedure described by Tsuchiya et al. [Proc. Natl. Acad. Sci. (1986) 83 7633]. For each chimera, the measurements are carried out between 3 and 6 times in a three-point test (three dilutions of the product) in a zone or the relation between the quantity of active product and incorporation of labelled thymidine (Amersham) is linear. In each microtitre plate, the activity of a reference product consisting of recombinant human G-CSF expressed in mammalian cells is also systematically incorporated. The results of FIG. 17 demonstrate that the chimera HSA-G.CSF (pYG1266) secreted by the yeast Kluyveromyces and purified according to Example E.9.3. is capable in vitro of transducing a signal for cellular proliferation for the line NFS60. In this particular case, the specific activity (cpm/molarity) of the chimera is about 7 times lower than that of the reference G-CSF (non-coupled).

E.11.2. Biological Activity In Vivo

The activity of stimulation of the HSA-G-CSF chimeras on granulopoiesis in vivo is tested after subcutaneous injection in rats (Sprague-Dawley/CD, 250–300 g, 8–9 weeks) and compared to that of the reference G-CSF expressed using mammalian cells. Each product, tested at the rate of 7 animals, is injected subcutaneously into the dorso-scapular region at the rate of 100 ml for 7 consecutive days, (D1–D7). 500 ml of blood are collected on days D-6, D2 (before the 2nd injection). D5 (before the 5th injection) and D8, and a blood count is performed. In this test, the specific activity (neutropoiesis units/mole injected) of the chimera HSA-G.CSF (pYG1266) is identical to that of the reference G-CSF (FIG. 18). Since this specific chimera has in vitro a specific activity 7 times lower than that of the reference G-CSF (FIG. 17), it is therefore demonstrated that the genetic coupling of G-CSF onto HSA favourably modifies the pharmacokinetic properties thereof.

We claim:

1. A fusion polypeptide comprising human serum albumin or a natural variant thereof and a separate, heterologous therapeutically active polypeptide attached to each of the C-terminal end and the N-terminal end of said human serum albumin.

2. A fusion polypeptide according to claim 1, wherein said therapeutically active polypeptide is of human origin.

3. A fusion protein according to claim 2, wherein the polypeptide attached to said C-terminal end of said albumin has the same chemical composition as that of the polypeptide attached to said N-terminal end of said albumin.

4. A fusion polypeptide according to claim 1, wherein said therapeutically active polypeptide comprises all or part of a polypeptide selected from the group consisting of enzymes, enzyme inhibitors, antigens, antibodies, hormones, coagulation factors, interferons, cytokines, growth factors, differentiation factors, factors involved in the genesis of bone tissues, factors involved in the resorption of bone factors, chemotactic factors, cell motility factors, migration factors, cytostatic factors, bactericidal factors, antifungal factors, plasma adhesive molecules, interstitial adhesive molecules and extracellular matrices.

5. A nucleotide sequence encoding a fusion polypeptide according to claim 1.

6. A nucleotide sequence according to claim 5, further comprising a leader sequence permitting the secretion of the expressed polypeptide.

7. An expression cassette comprising a nucleotide sequence according to claim 5 under the control of a promoter region.

8. A self-replicating vector comprising an expression cassette according to claim 7.

9. An expression cassette according to claim 7, further comprising a region for the termination of transcription.

10. A recombinant cell comprising a nucleotide sequence according to claim 5.

11. A recombinant cell according to claim 10, which is a yeast, an animal cell, a fungus or a bacterium.

12. A recombinant cell according to claim 11, which is a yeast.

13. A recombinant cell according to claim 12, which is a yeast of the genus Saccharomyces or Kluyveromyces.

14. A process for preparing a fusion polypeptide comprising a therapeutically active polypeptide fused to each of the C-terminal end and N-terminal end of human serum albumin or to a natural variant thereof, comprising culturing a recombinant cell of claim 10 under conditions for expression, and recovering the polypeptide produced.

15. A composition comprising a fusion polypeptide according to claim 1 and a pharmaceutically acceptable carrier.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
( A ) LENGTH: 1862 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: misc_feature
( B ) LOCATION: 1853..1855
( D ) OTHER INFORMATION: /note= "NNN is repeated p times"

( i x ) FEATURE:
( A ) NAME/KEY: CDS
( B ) LOCATION: 26..1858

( x i ) SEQUENCE DESCRIPTION: SEQ ID NO:1:

```
AAGCTTTACA ACAAATATAA AAACA ATG AAG TGG GTA ACC TTT ATT TCC CTT      52
                            Met Lys Trp Val Thr Phe Ile Ser Leu
                             1               5

CTT TTT CTC TTT AGC TCG GCT TAT TCC AGG GGT GTG TTT CGT CGA GAT     100
Leu Phe Leu Phe Ser Ser Ala Tyr Ser Arg Gly Val Phe Arg Arg Asp
 10                  15                  20                  25

GCA CAC AAG AGT GAG GTT GCT CAT CGG TTT AAA GAT TTG GGA GAA GAA     148
Ala His Lys Ser Glu Val Ala His Arg Phe Lys Asp Leu Gly Glu Glu
                 30                  35                  40

AAT TTC AAA GCC TTG GTG TTG ATT GCC TTT GCT CAG TAT CTT CAG CAG     196
Asn Phe Lys Ala Leu Val Leu Ile Ala Phe Ala Gln Tyr Leu Gln Gln
             45                  50                  55

TGT CCA TTT GAA GAT CAT GTA AAA TTA GTG AAT GAA GTA ACT GAA TTT     244
Cys Pro Phe Glu Asp His Val Lys Leu Val Asn Glu Val Thr Glu Phe
         60                  65                  70

GCA AAA ACA TGT GTT GCT GAT GAG TCA GCT GAA AAT TGT GAC AAA TCA     292
Ala Lys Thr Cys Val Ala Asp Glu Ser Ala Glu Asn Cys Asp Lys Ser
     75                  80                  85

CTT CAT ACC CTT TTT GGA GAC AAA TTA TGC ACA GTT GCA ACT CTT CGT     340
Leu His Thr Leu Phe Gly Asp Lys Leu Cys Thr Val Ala Thr Leu Arg
 90                  95                 100                 105

GAA ACC TAT GGT GAA ATG GCT GAC TGC TGT GCA AAA CAA GAA CCT GAG     388
Glu Thr Tyr Gly Glu Met Ala Asp Cys Cys Ala Lys Gln Glu Pro Glu
                110                 115                 120

AGA AAT GAA TGC TTC TTG CAA CAC AAA GAT GAC AAC CCA AAC CTC CCC     436
Arg Asn Glu Cys Phe Leu Gln His Lys Asp Asp Asn Pro Asn Leu Pro
            125                 130                 135

CGA TTG GTG AGA CCA GAG GTT GAT GTG ATG TGC ACT GCT TTT CAT GAC     484
Arg Leu Val Arg Pro Glu Val Asp Val Met Cys Thr Ala Phe His Asp
        140                 145                 150
```

-continued

```
AAT GAA GAG ACA TTT TTG AAA AAA TAC TTA TAT GAA ATT GCC AGA AGA     532
Asn Glu Glu Thr Phe Leu Lys Lys Tyr Leu Tyr Glu Ile Ala Arg Arg
    155                 160                 165

CAT CCT TAC TTT TAT GCC CCG GAA CTC CTT TTC TTT GCT AAA AGG TAT     580
His Pro Tyr Phe Tyr Ala Pro Glu Leu Leu Phe Phe Ala Lys Arg Tyr
170                 175                 180                 185

AAA GCT GCT TTT ACA GAA TGT TGC CAA GCT GCT GAT AAA GCT GCC TGC     628
Lys Ala Ala Phe Thr Glu Cys Cys Gln Ala Ala Asp Lys Ala Ala Cys
                190                 195                 200

CTG TTG CCA AAG CTC GAT GAA CTT CGG GAT GAA GGG AAG GCT TCG TCT     676
Leu Leu Pro Lys Leu Asp Glu Leu Arg Asp Glu Gly Lys Ala Ser Ser
            205                 210                 215

GCC AAA CAG AGA CTC AAG TGT GCC AGT CTC CAA AAA TTT GGA GAA AGA     724
Ala Lys Gln Arg Leu Lys Cys Ala Ser Leu Gln Lys Phe Gly Glu Arg
        220                 225                 230

GCT TTC AAA GCA TGG GCA GTA GCT CGC CTG AGC CAG AGA TTT CCC AAA     772
Ala Phe Lys Ala Trp Ala Val Ala Arg Leu Ser Gln Arg Phe Pro Lys
    235                 240                 245

GCT GAG TTT GCA GAA GTT TCC AAG TTA GTG ACA GAT CTT ACC AAA GTC     820
Ala Glu Phe Ala Glu Val Ser Lys Leu Val Thr Asp Leu Thr Lys Val
250                 255                 260                 265

CAC ACG GAA TGC TGC CAT GGA GAT CTG CTT GAA TGT GCT GAT GAC AGG     868
His Thr Glu Cys Cys His Gly Asp Leu Leu Glu Cys Ala Asp Asp Arg
                270                 275                 280

GCG GAC CTT GCC AAG TAT ATC TGT GAA AAT CAA GAT TCG ATC TCC AGT     916
Ala Asp Leu Ala Lys Tyr Ile Cys Glu Asn Gln Asp Ser Ile Ser Ser
            285                 290                 295

AAA CTG AAG GAA TGC TGT GAA AAA CCT CTG TTG GAA AAA TCC CAC TGC     964
Lys Leu Lys Glu Cys Cys Glu Lys Pro Leu Leu Glu Lys Ser His Cys
        300                 305                 310

ATT GCC GAA GTG GAA AAT GAT GAG ATG CCT GCT GAC TTG CCT TCA TTA    1012
Ile Ala Glu Val Glu Asn Asp Glu Met Pro Ala Asp Leu Pro Ser Leu
    315                 320                 325

GCT GCT GAT TTT GTT GAA AGT AAG GAT GTT TGC AAA AAC TAT GCT GAG    1060
Ala Ala Asp Phe Val Glu Ser Lys Asp Val Cys Lys Asn Tyr Ala Glu
330                 335                 340                 345

GCA AAG GAT GTC TTC CTG GGC ATG TTT TTG TAT GAA TAT GCA AGA AGG    1108
Ala Lys Asp Val Phe Leu Gly Met Phe Leu Tyr Glu Tyr Ala Arg Arg
                350                 355                 360

CAT CCT GAT TAC TCT GTC GTA CTG CTG CTG AGA CTT GCC AAG ACA TAT    1156
His Pro Asp Tyr Ser Val Val Leu Leu Leu Arg Leu Ala Lys Thr Tyr
            365                 370                 375

GAA ACC ACT CTA GAG AAG TGC TGT GCC GCT GCA GAT CCT CAT GAA TGC    1204
Glu Thr Thr Leu Glu Lys Cys Cys Ala Ala Ala Asp Pro His Glu Cys
        380                 385                 390

TAT GCC AAA GTG TTC GAT GAA TTT AAA CCT CTT GTG GAA GAG CCT CAG    1252
Tyr Ala Lys Val Phe Asp Glu Phe Lys Pro Leu Val Glu Glu Pro Gln
    395                 400                 405

AAT TTA ATC AAA CAA AAT TGT GAG CTT TTT GAG CAG CTT GGA GAG TAC    1300
Asn Leu Ile Lys Gln Asn Cys Glu Leu Phe Glu Gln Leu Gly Glu Tyr
410                 415                 420                 425

AAA TTC CAG AAT GCG CTA TTA GTT CGT TAC ACC AAG AAA GTA CCC CAA    1348
Lys Phe Gln Asn Ala Leu Leu Val Arg Tyr Thr Lys Lys Val Pro Gln
                430                 435                 440

GTG TCA ACT CCA ACT CTT GTA GAG GTC TCA AGA AAC CTA GGA AAA GTG    1396
Val Ser Thr Pro Thr Leu Val Glu Val Ser Arg Asn Leu Gly Lys Val
            445                 450                 455

GGC AGC AAA TGT TGT AAA CAT CCT GAA GCA AAA AGA ATG CCC TGT GCA    1444
Gly Ser Lys Cys Cys Lys His Pro Glu Ala Lys Arg Met Pro Cys Ala
        460                 465                 470
```

-continued

GAA GAC TAT CTA TCC GTG GTC CTG AAC CAG TTA TGT GTG TTG CAT GAG 1492
Glu Asp Tyr Leu Ser Val Val Leu Asn Gln Leu Cys Val Leu His Glu
475 480 485

AAA ACG CCA GTA AGT GAC AGA GTC ACC AAA TGC TGC ACA GAA TCC TTG 1540
Lys Thr Pro Val Ser Asp Arg Val Thr Lys Cys Cys Thr Glu Ser Leu
490 495 500 505

GTG AAC AGG CGA CCA TGC TTT TCA GCT CTG GAA GTC GAT GAA ACA TAC 1588
Val Asn Arg Arg Pro Cys Phe Ser Ala Leu Glu Val Asp Glu Thr Tyr
510 515 520

GTT CCC AAA GAG TTT AAT GCT GAA ACA TTC ACC TTC CAT GCA GAT ATA 1636
Val Pro Lys Glu Phe Asn Ala Glu Thr Phe Thr Phe His Ala Asp Ile
525 530 535

TGC ACA CTT TCT GAG AAG GAG AGA CAA ATC AAG AAA CAA ACT GCA CTT 1684
Cys Thr Leu Ser Glu Lys Glu Arg Gln Ile Lys Lys Gln Thr Ala Leu
540 545 550

GTT GAG CTT GTG AAA CAC AAG CCC AAG GCA ACA AAA GAG CAA CTG AAA 1732
Val Glu Leu Val Lys His Lys Pro Lys Ala Thr Lys Glu Gln Leu Lys
555 560 565

GCT GTT ATG GAT GAT TTC GCA GCT TTT GTA GAG AAG TGC TGC AAG GCT 1780
Ala Val Met Asp Asp Phe Ala Ala Phe Val Glu Lys Cys Cys Lys Ala
570 575 580 585

GAC GAT AAG GAG ACC TGC TTT GCC GAG GAG GGT AAA AAA CTT GTT GCT 1828
Asp Asp Lys Glu Thr Cys Phe Ala Glu Glu Gly Lys Lys Leu Val Ala
590 595 600

GCA AGT CAA GCT GCC TTA GGC TTA NNN TAAGCTT 1862
Ala Ser Gln Ala Ala Leu Gly Leu Xaa
605 610

( 2 ) INFORMATION FOR SEQ ID NO:2:

( i ) SEQUENCE CHARACTERISTICS:
( A ) LENGTH: 610 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Lys Trp Val Thr Phe Ile Ser Leu Leu Phe Leu Phe Ser Ser Ala
1 5 10 15

Tyr Ser Arg Gly Val Phe Arg Arg Asp Ala His Lys Ser Glu Val Ala
20 25 30

His Arg Phe Lys Asp Leu Gly Glu Glu Asn Phe Lys Ala Leu Val Leu
35 40 45

Ile Ala Phe Ala Gln Tyr Leu Gln Gln Cys Pro Phe Glu Asp His Val
50 55 60

Lys Leu Val Asn Glu Val Thr Glu Phe Ala Lys Thr Cys Val Ala Asp
65 70 75 80

Glu Ser Ala Glu Asn Cys Asp Lys Ser Leu His Thr Leu Phe Gly Asp
85 90 95

Lys Leu Cys Thr Val Ala Thr Leu Arg Glu Thr Tyr Gly Glu Met Ala
100 105 110

Asp Cys Cys Ala Lys Gln Glu Pro Glu Arg Asn Glu Cys Phe Leu Gln
115 120 125

His Lys Asp Asp Asn Pro Asn Leu Pro Arg Leu Val Arg Pro Glu Val
130 135 140

Asp Val Met Cys Thr Ala Phe His Asp Asn Glu Glu Thr Phe Leu Lys
145 150 155 160

Lys Tyr Leu Tyr Glu Ile Ala Arg Arg His Pro Tyr Phe Tyr Ala Pro
165 170 175

-continued

```
Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
```

```
             595                             600                             605

Leu Xaa
      610
```

( 2 ) INFORMATION FOR SEQ ID NO:3:

( i ) SEQUENCE CHARACTERISTICS:
( A ) LENGTH: 750 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 3..746

( x i ) SEQUENCE DESCRIPTION: SEQ ID NO:3:

```
CC TTA GGC TTA ACC TGT GAA GCC TGC CAG GAG CCG GGA GGC CTG GTG        47
   Leu Gly Leu Thr Cys Glu Ala Cys Gln Glu Pro Gly Gly Leu Val
     1               5                  10                  15

GTG CCT CCC ACA GAT GCC CCG GTG AGC CCC ACC ACT CTG TAT GTG GAG        95
Val Pro Pro Thr Asp Ala Pro Val Ser Pro Thr Thr Leu Tyr Val Glu
                 20                  25                  30

GAC ATC TCG GAA CCG CCG TTG CAC GAT TTC TAC TGC AGC AGG CTA CTG       143
Asp Ile Ser Glu Pro Pro Leu His Asp Phe Tyr Cys Ser Arg Leu Leu
             35                  40                  45

GAC CTG GTC TTC CTG CTG GAT GGC TCC TCC AGG CTG TCC GAG GCT GAG       191
Asp Leu Val Phe Leu Leu Asp Gly Ser Ser Arg Leu Ser Glu Ala Glu
         50                  55                  60

TTT GAA GTG CTG AAG GCC TTT GTG GTG GAC ATG ATG GAG CGG CTG CGC       239
Phe Glu Val Leu Lys Ala Phe Val Val Asp Met Met Glu Arg Leu Arg
     65                  70                  75

ATC TCC CAG AAG TGG GTC CGC GTG GCC GTG GTG GAG TAC CAC GAC GGC       287
Ile Ser Gln Lys Trp Val Arg Val Ala Val Val Glu Tyr His Asp Gly
 80                  85                  90                  95

TCC CAC GCC TAC ATC GGG CTC AAG GAC CGG AAG CGA CCG TCA GAG CTG       335
Ser His Ala Tyr Ile Gly Leu Lys Asp Arg Lys Arg Pro Ser Glu Leu
                100                 105                 110

CGG CGC ATT GCC AGC CAG GTG AAG TAT GCG GGC AGC CAG GTG GCC TCC       383
Arg Arg Ile Ala Ser Gln Val Lys Tyr Ala Gly Ser Gln Val Ala Ser
            115                 120                 125

ACC AGC GAG GTC TTG AAA TAC ACA CTG TTC CAA ATC TTC AGC AAG ATC       431
Thr Ser Glu Val Leu Lys Tyr Thr Leu Phe Gln Ile Phe Ser Lys Ile
        130                 135                 140

GAC CGC CCT GAA GCC TCC CGC ATC GCC CTG CTC CTG ATG GCC AGC CAG       479
Asp Arg Pro Glu Ala Ser Arg Ile Ala Leu Leu Leu Met Ala Ser Gln
    145                 150                 155

GAG CCC CAA CGG ATG TCC CGG AAC TTT GTC CGC TAC GTC CAG GGC CTG       527
Glu Pro Gln Arg Met Ser Arg Asn Phe Val Arg Tyr Val Gln Gly Leu
160                 165                 170                 175

AAG AAG AAG AAG GTC ATT GTG ATC CCG GTG GGC ATT GGG CCC CAT GCC       575
Lys Lys Lys Lys Val Ile Val Ile Pro Val Gly Ile Gly Pro His Ala
                180                 185                 190

AAC CTC AAG CAG ATC CGC CTC ATC GAG AAG CAG GCC CCT GAG AAC AAG       623
Asn Leu Lys Gln Ile Arg Leu Ile Glu Lys Gln Ala Pro Glu Asn Lys
            195                 200                 205

GCC TTC GTG CTG AGC AGT GTG GAT GAG CTG GAG CAG CAA AGG GAC GAG       671
Ala Phe Val Leu Ser Ser Val Asp Glu Leu Glu Gln Gln Arg Asp Glu
        210                 215                 220

ATC GTT AGC TAC CTC TGT GAC CTT GCC CCT GAA GCC CCT CCT CCT ACT       719
Ile Val Ser Tyr Leu Cys Asp Leu Ala Pro Glu Ala Pro Pro Pro Thr
```

```
      225                       230                       235

CTG  CCC  CCC  GAC  ATG  GCA  CAA  GTC  TAAGCTT                                   750
Leu  Pro  Pro  Asp  Met  Ala  Gln  Val
240                      245
```

( 2 ) INFORMATION FOR SEQ ID NO:4:

( i ) SEQUENCE CHARACTERISTICS:
( A ) LENGTH: 247 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Leu Gly Leu Thr Cys Glu Ala Cys Gln Glu Pro Gly Gly Leu Val Val
  1                 5                  10                  15

Pro Pro Thr Asp Ala Pro Val Ser Pro Thr Thr Leu Tyr Val Glu Asp
             20                  25                  30

Ile Ser Glu Pro Pro Leu His Asp Phe Tyr Cys Ser Arg Leu Leu Asp
         35                  40                  45

Leu Val Phe Leu Leu Asp Gly Ser Ser Arg Leu Ser Glu Ala Glu Phe
     50                  55                  60

Glu Val Leu Lys Ala Phe Val Val Asp Met Met Glu Arg Leu Arg Ile
 65                  70                  75                  80

Ser Gln Lys Trp Val Arg Val Ala Val Val Glu Tyr His Asp Gly Ser
                 85                  90                  95

His Ala Tyr Ile Gly Leu Lys Asp Arg Lys Arg Pro Ser Glu Leu Arg
            100                 105                 110

Arg Ile Ala Ser Gln Val Lys Tyr Ala Gly Ser Gln Val Ala Ser Thr
        115                 120                 125

Ser Glu Val Leu Lys Tyr Thr Leu Phe Gln Ile Phe Ser Lys Ile Asp
    130                 135                 140

Arg Pro Glu Ala Ser Arg Ile Ala Leu Leu Leu Met Ala Ser Gln Glu
145                 150                 155                 160

Pro Gln Arg Met Ser Arg Asn Phe Val Arg Tyr Val Gln Gly Leu Lys
                165                 170                 175

Lys Lys Lys Val Ile Val Ile Pro Val Gly Ile Gly Pro His Ala Asn
            180                 185                 190

Leu Lys Gln Ile Arg Leu Ile Glu Lys Gln Ala Pro Glu Asn Lys Ala
        195                 200                 205

Phe Val Leu Ser Ser Val Asp Glu Leu Glu Gln Gln Arg Asp Glu Ile
    210                 215                 220

Val Ser Tyr Leu Cys Asp Leu Ala Pro Glu Ala Pro Pro Pro Thr Leu
225                 230                 235                 240

Pro Pro Asp Met Ala Gln Val
                245
```

( 2 ) INFORMATION FOR SEQ ID NO:5:

( i ) SEQUENCE CHARACTERISTICS:
( A ) LENGTH: 105 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 3..101

(xi) SEQUENCE DESCRIPTION: SEQ ID NO:5:

```
CC TTA GGC TTA ACC TGT GAA GCC TGC CAG GAG CCG GGA GGC CTG GTG       47
   Leu Gly Leu Thr Cys Glu Ala Cys Gln Glu Pro Gly Gly Leu Val
    1               5                  10                  15

GTG CCT CCC ACA GAT GCC CCG GTG AGC CCC ACC ACT CTG TAT GTG GAG      95
Val Pro Pro Thr Asp Ala Pro Val Ser Pro Thr Thr Leu Tyr Val Glu
                20                  25                  30

GAC TAAGCTT                                                         105
Asp
```

(2) INFORMATION FOR SEQ ID NO:6:

(i) SEQUENCE CHARACTERISTICS:
(A) LENGTH: 32 amino acids
(B) TYPE: amino acid
(D) TOPOLOGY: linear (ii) MOLECULE TYPE: protein (xi) SEQUENCE DESCRIPTION: SEQ ID NO:6:

```
Leu Gly Leu Thr Cys Glu Ala Cys Gln Glu Pro Gly Gly Leu Val Val
 1               5                  10                  15

Pro Pro Thr Asp Ala Pro Val Ser Pro Thr Thr Leu Tyr Val Glu Asp
            20                  25                  30
```

(2) INFORMATION FOR SEQ ID NO:7:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..56

(xi) SEQUENCE DESCRIPTION: SEQ ID NO:7:

```
CC TTA GGC CTC TGT GAC CTT GCC CCT GAA GCC CCT CCT CCT ACT CTG       47
   Leu Gly Leu Cys Asp Leu Ala Pro Glu Ala Pro Pro Pro Thr Leu
    1               5                  10                  15

CCC CCC TAAGCTT                                                      60
Pro Pro
```

(2) INFORMATION FOR SEQ ID NO:8:

(i) SEQUENCE CHARACTERISTICS:
(A) LENGTH: 17 amino acids
(B) TYPE: amino acid
(D) TOPOLOGY: linear (ii) MOLECULE TYPE: protein (xi) SEQUENCE DESCRIPTION: SEQ ID NO:8:

```
Leu Gly Leu Cys Asp Leu Ala Pro Glu Ala Pro Pro Pro Thr Leu Pro
 1               5                  10                  15

Pro
```

(2) INFORMATION FOR SEQ ID NO:9:

(i) SEQUENCE CHARACTERISTICS:
(A) LENGTH: 288 base pairs
(B) TYPE: nucleic acid
(C) STRANDEDNESS: double (D) TOPOLOGY: linear (ii) MOLECULE TYPE: cDNA (ix) FEATURE:
(A) NAME/KEY: CDS
(B) LOCATION: 3..284

(xi) SEQUENCE DESCRIPTION: SEQ ID NO:9:

```
CC TTA GGC TTA ACC TGT GAA GCC TGC CAG GAG CCG GGA GGC CTG GTG      47
   Leu Gly Leu Thr Cys Glu Ala Cys Gln Glu Pro Gly Gly Leu Val
    1               5                  10                  15

GTG CCT CCC ACA GAT GCC CCG GTG AGC CCC ACC ACT CTG TAT GTG GAG     95
Val Pro Pro Thr Asp Ala Pro Val Ser Pro Thr Thr Leu Tyr Val Glu
                20                  25                  30

GAC ATC TCG GAA CCG CCG TTG CAC GAT TTC TAC CGC CTC ATC GAG AAG    143
Asp Ile Ser Glu Pro Pro Leu His Asp Phe Tyr Arg Leu Ile Glu Lys
            35                  40                  45

CAG GCC CCT GAG AAC AAG GCC TTC GTG CTG AGC AGT GTG GAT GAG CTG    191
Gln Ala Pro Glu Asn Lys Ala Phe Val Leu Ser Ser Val Asp Glu Leu
        50                  55                  60

GAG CAG CAA AGG GAC GAG ATC GTT AGC TAC CTC TGT GAC CTT GCC CCT    239
Glu Gln Gln Arg Asp Glu Ile Val Ser Tyr Leu Cys Asp Leu Ala Pro
    65                  70                  75

GAA GCC CCT CCT CCT ACT CTG CCC CCC GAC ATG GCA CAA GTC TAAGCTT    288
Glu Ala Pro Pro Pro Thr Leu Pro Pro Asp Met Ala Gln Val
80                  85                  90
```

(2) INFORMATION FOR SEQ ID NO:10:

(i) SEQUENCE CHARACTERISTICS:
(A) LENGTH: 93 amino acids
(B) TYPE: amino acid
(D) TOPOLOGY: linear (ii) MOLECULE TYPE: protein (xi) SEQUENCE DESCRIPTION: SEQ ID NO:10:

```
Leu Gly Leu Thr Cys Glu Ala Cys Gln Glu Pro Gly Gly Leu Val Val
 1               5                  10                  15

Pro Pro Thr Asp Ala Pro Val Ser Pro Thr Thr Leu Tyr Val Glu Asp
            20                  25                  30

Ile Ser Glu Pro Pro Leu His Asp Phe Tyr Arg Leu Ile Glu Lys Gln
        35                  40                  45

Ala Pro Glu Asn Lys Ala Phe Val Leu Ser Ser Val Asp Glu Leu Glu
    50                  55                  60

Gln Gln Arg Asp Glu Ile Val Ser Tyr Leu Cys Asp Leu Ala Pro Glu
65                  70                  75                  80

Ala Pro Pro Pro Thr Leu Pro Pro Asp Met Ala Gln Val
                85                  90
```

(2) INFORMATION FOR SEQ ID NO:11:

(i) SEQUENCE CHARACTERISTICS:
(A) LENGTH: 423 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..419

(xi) SEQUENCE DESCRIPTION: SEQ ID NO:11:

```
CC TTA GGC TTA AGC AAT GAA CTT CAT CAA GTT CCA TCG AAC TGT GAC          47
   Leu Gly Leu Ser Asn Glu Leu His Gln Val Pro Ser Asn Cys Asp
    1               5                  10                  15

TGT CTA AAT GGA GGA ACA TGT GTG TCC AAC AAG TAC TTC TCC AAC ATT         95
Cys Leu Asn Gly Gly Thr Cys Val Ser Asn Lys Tyr Phe Ser Asn Ile
                20                  25                  30

CAC TGG TGC AAC TGC CCA AAG AAA TTC GGA GGG CAG CAC TGT GAA ATA        143
His Trp Cys Asn Cys Pro Lys Lys Phe Gly Gly Gln His Cys Glu Ile
            35                  40                  45

GAT AAG TCA AAA ACC TGC TAT GAG GGG AAT GGT CAC TTT TAC CGA GGA        191
Asp Lys Ser Lys Thr Cys Tyr Glu Gly Asn Gly His Phe Tyr Arg Gly
        50                  55                  60

AAG GCC AGC ACT GAC ACC ATG GGC CGG CCC TGC CTG CCC TGG AAC TCT        239
Lys Ala Ser Thr Asp Thr Met Gly Arg Pro Cys Leu Pro Trp Asn Ser
    65                  70                  75

GCC ACT GTC CTT CAG CAA ACG TAC CAT GCC CAC AGA TCT GAT GCT CTT        287
Ala Thr Val Leu Gln Gln Thr Tyr His Ala His Arg Ser Asp Ala Leu
80                  85                  90                  95

CAG CTG GGC CTG GGG AAA CAT AAT TAC TGC AGG AAC CCA GAC AAC CGG        335
Gln Leu Gly Leu Gly Lys His Asn Tyr Cys Arg Asn Pro Asp Asn Arg
                100                 105                 110

AGG CGA CCC TGG TGC TAT GTG CAG GTG GGC CTA AAG CCG CTT GTC CAA        383
Arg Arg Pro Trp Cys Tyr Val Gln Val Gly Leu Lys Pro Leu Val Gln
            115                 120                 125

GAG TGC ATG GTG CAT GAC TGC GCA GAT GGA AAA TAAGCTT                    423
Glu Cys Met Val His Asp Cys Ala Asp Gly Lys
        130                 135
```

( 2 ) INFORMATION FOR SEQ ID NO:12:

( i ) SEQUENCE CHARACTERISTICS:
( A ) LENGTH: 138 amino acids
( B ) TYPE: amino acid
( D ) TOPOLOGY: linear ( i i ) MOLECULE TYPE: protein ( x i ) SEQUENCE DESCRIPTION: SEQ ID NO:12:

```
Leu Gly Leu Ser Asn Glu Leu His Gln Val Pro Ser Asn Cys Asp Cys
1               5                   10                  15

Leu Asn Gly Gly Thr Cys Val Ser Asn Lys Tyr Phe Ser Asn Ile His
            20                  25                  30

Trp Cys Asn Cys Pro Lys Lys Phe Gly Gly Gln His Cys Glu Ile Asp
        35                  40                  45

Lys Ser Lys Thr Cys Tyr Glu Gly Asn Gly His Phe Tyr Arg Gly Lys
    50                  55                  60

Ala Ser Thr Asp Thr Met Gly Arg Pro Cys Leu Pro Trp Asn Ser Ala
65                  70                  75                  80

Thr Val Leu Gln Gln Thr Tyr His Ala His Arg Ser Asp Ala Leu Gln
                85                  90                  95

Leu Gly Leu Gly Lys His Asn Tyr Cys Arg Asn Pro Asp Asn Arg Arg
            100                 105                 110

Arg Pro Trp Cys Tyr Val Gln Val Gly Leu Lys Pro Leu Val Gln Glu
        115                 120                 125

Cys Met Val His Asp Cys Ala Asp Gly Lys
    130                 135
```

( 2 ) INFORMATION FOR SEQ ID NO:13:

( i ) SEQUENCE CHARACTERISTICS:

(A) LENGTH: 541 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 3..536

(xi) SEQUENCE DESCRIPTION: SEQ ID NO:13:

```
CC TTA GGC TTA ACC CCC CTG GGC CCT GCC AGC TCC CTG CCC CAG AGC      47
   Leu Gly Leu Thr Pro Leu Gly Pro Ala Ser Ser Leu Pro Gln Ser
     1               5                  10                  15

TTC CTG CTC AAG TGC TTA GAG CAA GTG AGG AAG ATC CAG GGC GAT GGC     95
Phe Leu Leu Lys Cys Leu Glu Gln Val Arg Lys Ile Gln Gly Asp Gly
                20                  25                  30

GCA GCG CTC CAG GAG AAG CTG TGT GCC ACC TAC AAG CTG TGC CAC CCC    143
Ala Ala Leu Gln Glu Lys Leu Cys Ala Thr Tyr Lys Leu Cys His Pro
            35                  40                  45

GAG GAG CTG GTG CTG CTC GGA CAC TCT CTG GGC ATC CCC TGG GCT CCC    191
Glu Glu Leu Val Leu Leu Gly His Ser Leu Gly Ile Pro Trp Ala Pro
        50                  55                  60

CTG AGC TCC TGC CCC AGC CAG GCC CTG CAG CTG GCA GGC TGC TTG AGC    239
Leu Ser Ser Cys Pro Ser Gln Ala Leu Gln Leu Ala Gly Cys Leu Ser
    65                  70                  75

CAA CTC CAT AGC GGC CTT TTC CTC TAC CAG GGG CTC CTG CAG GCC CTG    287
Gln Leu His Ser Gly Leu Phe Leu Tyr Gln Gly Leu Leu Gln Ala Leu
 80                  85                  90                  95

GAA GGG ATA TCC CCC GAG TTG GGT CCC ACC TTG GAC ACA CTG CAG CTG    335
Glu Gly Ile Ser Pro Glu Leu Gly Pro Thr Leu Asp Thr Leu Gln Leu
                100                 105                 110

GAC GTC GCC GAC TTT GCC ACC ACC ATC TGG CAG CAG ATG GAA GAA CTG    383
Asp Val Ala Asp Phe Ala Thr Thr Ile Trp Gln Gln Met Glu Glu Leu
            115                 120                 125

GGA ATG GCC CCT GCC CTG CAG CCC ACC CAG GGT GCC ATG CCG GCC TTC    431
Gly Met Ala Pro Ala Leu Gln Pro Thr Gln Gly Ala Met Pro Ala Phe
        130                 135                 140

GCC TCT GCT TTC CAG CGC CGG GCA GGA GGG GTC CTG GTT GCT AGC CAT    479
Ala Ser Ala Phe Gln Arg Arg Ala Gly Gly Val Leu Val Ala Ser His
    145                 150                 155

CTG CAG AGC TTC CTG GAG GTG TCG TAC CGC GTT CTA CGC CAC CTT GCG    527
Leu Gln Ser Phe Leu Glu Val Ser Tyr Arg Val Leu Arg His Leu Ala
160                 165                 170                 175

CAG CCC TGAAGCTT                                                   541
Gln Pro
```

(2) INFORMATION FOR SEQ ID NO:14:

(i) SEQUENCE CHARACTERISTICS:
(A) LENGTH: 177 amino acids
(B) TYPE: amino acid
(D) TOPOLOGY: linear (ii) MOLECULE TYPE: protein (xi) SEQUENCE DESCRIPTION: SEQ ID NO:14:

```
Leu Gly Leu Thr Pro Leu Gly Pro Ala Ser Ser Leu Pro Gln Ser Phe
  1               5                  10                  15

Leu Leu Lys Cys Leu Glu Gln Val Arg Lys Ile Gln Gly Asp Gly Ala
            20                  25                  30

Ala Leu Gln Glu Lys Leu Cys Ala Thr Tyr Lys Leu Cys His Pro Glu
        35                  40                  45
```

```
Glu Leu Val Leu Leu Gly His Ser Leu Gly Ile Pro Trp Ala Pro Leu
     50                  55                  60

Ser Ser Cys Pro Ser Gln Ala Leu Gln Leu Ala Gly Cys Leu Ser Gln
 65                  70                  75                      80

Leu His Ser Gly Leu Phe Leu Tyr Gln Gly Leu Leu Gln Ala Leu Glu
                 85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
    130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro
```

( 2 ) INFORMATION FOR SEQ ID NO:15:

( i ) SEQUENCE CHARACTERISTICS:
( A ) LENGTH: 2455 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 26..2389

( x i ) SEQUENCE DESCRIPTION: SEQ ID NO:15:

```
AAGCTTTACA ACAAATATAA AAACA ATG AAG TGG GTA ACC TTT ATT TCC CTT      52
                            Met Lys Trp Val Thr Phe Ile Ser Leu
                              1               5

CTT TTT CTC TTT AGC TCG GCT TAT TCC AGG GGT GTG TTT CGT CGA ACC     100
Leu Phe Leu Phe Ser Ser Ala Tyr Ser Arg Gly Val Phe Arg Arg Thr
 10                  15                  20                  25

CCC CTG GGC CCT GCC AGC TCC CTG CCC CAG AGC TTC CTG CTC AAG TGC     148
Pro Leu Gly Pro Ala Ser Ser Leu Pro Gln Ser Phe Leu Leu Lys Cys
                 30                  35                  40

TTA GAG CAA GTG AGG AAG ATC CAG GGC GAT GGC GCA GCG CTC CAG GAG     196
Leu Glu Gln Val Arg Lys Ile Gln Gly Asp Gly Ala Ala Leu Gln Glu
             45                  50                  55

AAG CTG TGT GCC ACC TAC AAG CTG TGC CAC CCC GAG GAG CTG GTG CTG     244
Lys Leu Cys Ala Thr Tyr Lys Leu Cys His Pro Glu Glu Leu Val Leu
         60                  65                  70

CTC GGA CAC TCT CTG GGC ATC CCC TGG GCT CCC CTG AGC TCC TGC CCC     292
Leu Gly His Ser Leu Gly Ile Pro Trp Ala Pro Leu Ser Ser Cys Pro
     75                  80                  85

AGC CAG GCC CTG CAG CTG GCA GGC TGC TTG AGC CAA CTC CAT AGC GGC     340
Ser Gln Ala Leu Gln Leu Ala Gly Cys Leu Ser Gln Leu His Ser Gly
 90                  95                 100                 105

CTT TTC CTC TAC CAG GGG CTC CTG CAG GCC CTG GAA GGG ATA TCC CCC     388
Leu Phe Leu Tyr Gln Gly Leu Leu Gln Ala Leu Glu Gly Ile Ser Pro
                110                 115                 120

GAG TTG GGT CCC ACC TTG GAC ACA CTG CAG CTG GAC GTC GCC GAC TTT     436
Glu Leu Gly Pro Thr Leu Asp Thr Leu Gln Leu Asp Val Ala Asp Phe
            125                 130                 135
```

-continued

```
GCC ACC ACC ATC TGG CAG CAG ATG GAA GAA CTG GGA ATG GCC CCT GCC      484
Ala Thr Thr Ile Trp Gln Gln Met Glu Glu Leu Gly Met Ala Pro Ala
        140                 145                 150

CTG CAG CCC ACC CAG GGT GCC ATG CCG GCC TTC GCC TCT GCT TTC CAG      532
Leu Gln Pro Thr Gln Gly Ala Met Pro Ala Phe Ala Ser Ala Phe Gln
    155                 160                 165

CGC CGG GCA GGA GGG GTC CTG GTT GCT AGC CAT CTG CAG AGC TTC CTG      580
Arg Arg Ala Gly Gly Val Leu Val Ala Ser His Leu Gln Ser Phe Leu
170                 175                 180                 185

GAG GTG TCG TAC CGC GTT CTA CGC CAC CTT GCG CAG CCC GGT GGA GGC      628
Glu Val Ser Tyr Arg Val Leu Arg His Leu Ala Gln Pro Gly Gly Gly
                190                 195                 200

GGT GAT GCA CAC AAG AGT GAG GTT GCT CAT CGG TTT AAA GAT TTG GGA      676
Gly Asp Ala His Lys Ser Glu Val Ala His Arg Phe Lys Asp Leu Gly
            205                 210                 215

GAA GAA AAT TTC AAA GCC TTG GTG TTG ATT GCC TTT GCT CAG TAT CTT      724
Glu Glu Asn Phe Lys Ala Leu Val Leu Ile Ala Phe Ala Gln Tyr Leu
        220                 225                 230

CAG CAG TGT CCA TTT GAA GAT CAT GTA AAA TTA GTG AAT GAA GTA ACT      772
Gln Gln Cys Pro Phe Glu Asp His Val Lys Leu Val Asn Glu Val Thr
    235                 240                 245

GAA TTT GCA AAA ACA TGT GTT GCT GAT GAG TCA GCT GAA AAT TGT GAC      820
Glu Phe Ala Lys Thr Cys Val Ala Asp Glu Ser Ala Glu Asn Cys Asp
250                 255                 260                 265

AAA TCA CTT CAT ACC CTT TTT GGA GAC AAA TTA TGC ACA GTT GCA ACT      868
Lys Ser Leu His Thr Leu Phe Gly Asp Lys Leu Cys Thr Val Ala Thr
                270                 275                 280

CTT CGT GAA ACC TAT GGT GAA ATG GCT GAC TGC TGT GCA AAA CAA GAA      916
Leu Arg Glu Thr Tyr Gly Glu Met Ala Asp Cys Cys Ala Lys Gln Glu
            285                 290                 295

CCT GAG AGA AAT GAA TGC TTC TTG CAA CAC AAA GAT GAC AAC CCA AAC      964
Pro Glu Arg Asn Glu Cys Phe Leu Gln His Lys Asp Asp Asn Pro Asn
        300                 305                 310

CTC CCC CGA TTG GTG AGA CCA GAG GTT GAT GTG ATG TGC ACT GCT TTT     1012
Leu Pro Arg Leu Val Arg Pro Glu Val Asp Val Met Cys Thr Ala Phe
    315                 320                 325

CAT GAC AAT GAA GAG ACA TTT TTG AAA AAA TAC TTA TAT GAA ATT GCC     1060
His Asp Asn Glu Glu Thr Phe Leu Lys Lys Tyr Leu Tyr Glu Ile Ala
330                 335                 340                 345

AGA AGA CAT CCT TAC TTT TAT GCC CCG GAA CTC CTT TTC TTT GCT AAA     1108
Arg Arg His Pro Tyr Phe Tyr Ala Pro Glu Leu Leu Phe Phe Ala Lys
                350                 355                 360

AGG TAT AAA GCT GCT TTT ACA GAA TGT TGC CAA GCT GCT GAT AAA GCT     1156
Arg Tyr Lys Ala Ala Phe Thr Glu Cys Cys Gln Ala Ala Asp Lys Ala
            365                 370                 375

GCC TGC CTG TTG CCA AAG CTC GAT GAA CTT CGG GAT GAA GGG AAG GCT     1204
Ala Cys Leu Leu Pro Lys Leu Asp Glu Leu Arg Asp Glu Gly Lys Ala
        380                 385                 390

TCG TCT GCC AAA CAG AGA CTC AAG TGT GCC AGT CTC CAA AAA TTT GGA     1252
Ser Ser Ala Lys Gln Arg Leu Lys Cys Ala Ser Leu Gln Lys Phe Gly
    395                 400                 405

GAA AGA GCT TTC AAA GCA TGG GCA GTA GCT CGC CTG AGC CAG AGA TTT     1300
Glu Arg Ala Phe Lys Ala Trp Ala Val Ala Arg Leu Ser Gln Arg Phe
410                 415                 420                 425

CCC AAA GCT GAG TTT GCA GAA GTT TCC AAG TTA GTG ACA GAT CTT ACC     1348
Pro Lys Ala Glu Phe Ala Glu Val Ser Lys Leu Val Thr Asp Leu Thr
                430                 435                 440

AAA GTC CAC ACG GAA TGC TGC CAT GGA GAT CTG CTT GAA TGT GCT GAT     1396
Lys Val His Thr Glu Cys Cys His Gly Asp Leu Leu Glu Cys Ala Asp
            445                 450                 455
```

-continued

```
GAC AGG GCG GAC CTT GCC AAG TAT ATC TGT GAA AAT CAA GAT TCG ATC    1444
Asp Arg Ala Asp Leu Ala Lys Tyr Ile Cys Glu Asn Gln Asp Ser Ile
        460                 465                 470

TCC AGT AAA CTG AAG GAA TGC TGT GAA AAA CCT CTG TTG GAA AAA TCC    1492
Ser Ser Lys Leu Lys Glu Cys Cys Glu Lys Pro Leu Leu Glu Lys Ser
    475                 480                 485

CAC TGC ATT GCC GAA GTG GAA AAT GAT GAG ATG CCT GCT GAC TTG CCT    1540
His Cys Ile Ala Glu Val Glu Asn Asp Glu Met Pro Ala Asp Leu Pro
490                 495                 500                 505

TCA TTA GCT GCT GAT TTT GTT GAA AGT AAG GAT GTT TGC AAA AAC TAT    1588
Ser Leu Ala Ala Asp Phe Val Glu Ser Lys Asp Val Cys Lys Asn Tyr
                510                 515                 520

GCT GAG GCA AAG GAT GTC TTC CTG GGC ATG TTT TTG TAT GAA TAT GCA    1636
Ala Glu Ala Lys Asp Val Phe Leu Gly Met Phe Leu Tyr Glu Tyr Ala
            525                 530                 535

AGA AGG CAT CCT GAT TAC TCT GTC GTA CTG CTG CTG AGA CTT GCC AAG    1684
Arg Arg His Pro Asp Tyr Ser Val Val Leu Leu Leu Arg Leu Ala Lys
        540                 545                 550

ACA TAT GAA ACC ACT CTA GAG AAG TGC TGT GCC GCT GCA GAT CCT CAT    1732
Thr Tyr Glu Thr Thr Leu Glu Lys Cys Cys Ala Ala Ala Asp Pro His
    555                 560                 565

GAA TGC TAT GCC AAA GTG TTC GAT GAA TTT AAA CCT CTT GTG GAA GAG    1780
Glu Cys Tyr Ala Lys Val Phe Asp Glu Phe Lys Pro Leu Val Glu Glu
570                 575                 580                 585

CCT CAG AAT TTA ATC AAA CAA AAT TGT GAG CTT TTT GAG CAG CTT GGA    1828
Pro Gln Asn Leu Ile Lys Gln Asn Cys Glu Leu Phe Glu Gln Leu Gly
                590                 595                 600

GAG TAC AAA TTC CAG AAT GCG CTA TTA GTT CGT TAC ACC AAG AAA GTA    1876
Glu Tyr Lys Phe Gln Asn Ala Leu Leu Val Arg Tyr Thr Lys Lys Val
            605                 610                 615

CCC CAA GTG TCA ACT CCA ACT CTT GTA GAG GTC TCA AGA AAC CTA GGA    1924
Pro Gln Val Ser Thr Pro Thr Leu Val Glu Val Ser Arg Asn Leu Gly
        620                 625                 630

AAA GTG GGC AGC AAA TGT TGT AAA CAT CCT GAA GCA AAA AGA ATG CCC    1972
Lys Val Gly Ser Lys Cys Cys Lys His Pro Glu Ala Lys Arg Met Pro
    635                 640                 645

TGT GCA GAA GAC TAT CTA TCC GTG GTC CTG AAC CAG TTA TGT GTG TTG    2020
Cys Ala Glu Asp Tyr Leu Ser Val Val Leu Asn Gln Leu Cys Val Leu
650                 655                 660                 665

CAT GAG AAA ACG CCA GTA AGT GAC AGA GTC ACC AAA TGC TGC ACA GAA    2068
His Glu Lys Thr Pro Val Ser Asp Arg Val Thr Lys Cys Cys Thr Glu
                670                 675                 680

TCC TTG GTG AAC AGG CGA CCA TGC TTT TCA GCT CTG GAA GTC GAT GAA    2116
Ser Leu Val Asn Arg Arg Pro Cys Phe Ser Ala Leu Glu Val Asp Glu
            685                 690                 695

ACA TAC GTT CCC AAA GAG TTT AAT GCT GAA ACA TTC ACC TTC CAT GCA    2164
Thr Tyr Val Pro Lys Glu Phe Asn Ala Glu Thr Phe Thr Phe His Ala
        700                 705                 710

GAT ATA TGC ACA CTT TCT GAG AAG GAG AGA CAA ATC AAG AAA CAA ACT    2212
Asp Ile Cys Thr Leu Ser Glu Lys Glu Arg Gln Ile Lys Lys Gln Thr
    715                 720                 725

GCA CTT GTT GAG CTT GTG AAA CAC AAG CCC AAG GCA ACA AAA GAG CAA    2260
Ala Leu Val Glu Leu Val Lys His Lys Pro Lys Ala Thr Lys Glu Gln
730                 735                 740                 745

CTG AAA GCT GTT ATG GAT GAT TTC GCA GCT TTT GTA GAG AAG TGC TGC    2308
Leu Lys Ala Val Met Asp Asp Phe Ala Ala Phe Val Glu Lys Cys Cys
                750                 755                 760

AAG GCT GAC GAT AAG GAG ACC TGC TTT GCC GAG GAG GGT AAA AAA CTT    2356
Lys Ala Asp Asp Lys Glu Thr Cys Phe Ala Glu Glu Gly Lys Lys Leu
            765                 770                 775
```

```
GTT GCT GCA AGT CAA GCT GCC TTA GGC TTA TAACATCACA TTTAAAGCA          2406
Val Ala Ala Ser Gln Ala Ala Leu Gly Leu
        780                 785

TCTCAGCCTA CCATGAGAAT AAGAGAAAGA AAATGAAGAT CAAAAGCTT                 2455
```

( 2 ) INFORMATION FOR SEQ ID NO:16:

( i ) SEQUENCE CHARACTERISTICS:
( A ) LENGTH: 787 amino acids
( B ) TYPE: amino acid
( D ) TOPOLOGY: linear ( i i ) MOLECULE TYPE: protein ( x i ) SEQUENCE DESCRIPTION: SEQ ID NO:16:

```
Met Lys Trp Val Thr Phe Ile Ser Leu Leu Phe Leu Phe Ser Ser Ala
  1                 5                  10                  15

Tyr Ser Arg Gly Val Phe Arg Arg Thr Pro Leu Gly Pro Ala Ser Ser
             20                  25                  30

Leu Pro Gln Ser Phe Leu Leu Lys Cys Leu Glu Gln Val Arg Lys Ile
         35                  40                  45

Gln Gly Asp Gly Ala Ala Leu Gln Glu Lys Leu Cys Ala Thr Tyr Lys
     50                  55                  60

Leu Cys His Pro Glu Glu Leu Val Leu Leu Gly His Ser Leu Gly Ile
 65                  70                  75                  80

Pro Trp Ala Pro Leu Ser Ser Cys Pro Ser Gln Ala Leu Gln Leu Ala
                 85                  90                  95

Gly Cys Leu Ser Gln Leu His Ser Gly Leu Phe Leu Tyr Gln Gly Leu
            100                 105                 110

Leu Gln Ala Leu Glu Gly Ile Ser Pro Glu Leu Gly Pro Thr Leu Asp
        115                 120                 125

Thr Leu Gln Leu Asp Val Ala Asp Phe Ala Thr Thr Ile Trp Gln Gln
    130                 135                 140

Met Glu Glu Leu Gly Met Ala Pro Ala Leu Gln Pro Thr Gln Gly Ala
145                 150                 155                 160

Met Pro Ala Phe Ala Ser Ala Phe Gln Arg Arg Ala Gly Gly Val Leu
                165                 170                 175

Val Ala Ser His Leu Gln Ser Phe Leu Glu Val Ser Tyr Arg Val Leu
            180                 185                 190

Arg His Leu Ala Gln Pro Gly Gly Gly Gly Asp Ala His Lys Ser Glu
        195                 200                 205

Val Ala His Arg Phe Lys Asp Leu Gly Glu Glu Asn Phe Lys Ala Leu
    210                 215                 220

Val Leu Ile Ala Phe Ala Gln Tyr Leu Gln Gln Cys Pro Phe Glu Asp
225                 230                 235                 240

His Val Lys Leu Val Asn Glu Val Thr Glu Phe Ala Lys Thr Cys Val
                245                 250                 255

Ala Asp Glu Ser Ala Glu Asn Cys Asp Lys Ser Leu His Thr Leu Phe
            260                 265                 270

Gly Asp Lys Leu Cys Thr Val Ala Thr Leu Arg Glu Thr Tyr Gly Glu
        275                 280                 285

Met Ala Asp Cys Cys Ala Lys Gln Glu Pro Glu Arg Asn Glu Cys Phe
    290                 295                 300

Leu Gln His Lys Asp Asp Asn Pro Asn Leu Pro Arg Leu Val Arg Pro
305                 310                 315                 320

Glu Val Asp Val Met Cys Thr Ala Phe His Asp Asn Glu Glu Thr Phe
                325                 330                 335
```

Leu Lys Lys Tyr Leu Tyr Glu Ile Ala Arg Arg His Pro Tyr Phe Tyr
340 345 350

Ala Pro Glu Leu Leu Phe Phe Ala Lys Arg Tyr Lys Ala Ala Phe Thr
355 360 365

Glu Cys Cys Gln Ala Ala Asp Lys Ala Ala Cys Leu Leu Pro Lys Leu
370 375 380

Asp Glu Leu Arg Asp Glu Gly Lys Ala Ser Ser Ala Lys Gln Arg Leu
385 390 395 400

Lys Cys Ala Ser Leu Gln Lys Phe Gly Glu Arg Ala Phe Lys Ala Trp
405 410 415

Ala Val Ala Arg Leu Ser Gln Arg Phe Pro Lys Ala Glu Phe Ala Glu
420 425 430

Val Ser Lys Leu Val Thr Asp Leu Thr Lys Val His Thr Glu Cys Cys
435 440 445

His Gly Asp Leu Leu Glu Cys Ala Asp Asp Arg Ala Asp Leu Ala Lys
450 455 460

Tyr Ile Cys Glu Asn Gln Asp Ser Ile Ser Ser Lys Leu Lys Glu Cys
465 470 475 480

Cys Glu Lys Pro Leu Leu Glu Lys Ser His Cys Ile Ala Glu Val Glu
485 490 495

Asn Asp Glu Met Pro Ala Asp Leu Pro Ser Leu Ala Ala Asp Phe Val
500 505 510

Glu Ser Lys Asp Val Cys Lys Asn Tyr Ala Glu Ala Lys Asp Val Phe
515 520 525

Leu Gly Met Phe Leu Tyr Glu Tyr Ala Arg Arg His Pro Asp Tyr Ser
530 535 540

Val Val Leu Leu Leu Arg Leu Ala Lys Thr Tyr Glu Thr Thr Leu Glu
545 550 555 560

Lys Cys Cys Ala Ala Ala Asp Pro His Glu Cys Tyr Ala Lys Val Phe
565 570 575

Asp Glu Phe Lys Pro Leu Val Glu Glu Pro Gln Asn Leu Ile Lys Gln
580 585 590

Asn Cys Glu Leu Phe Glu Gln Leu Gly Glu Tyr Lys Phe Gln Asn Ala
595 600 605

Leu Leu Val Arg Tyr Thr Lys Lys Val Pro Gln Val Ser Thr Pro Thr
610 615 620

Leu Val Glu Val Ser Arg Asn Leu Gly Lys Val Gly Ser Lys Cys Cys
625 630 635 640

Lys His Pro Glu Ala Lys Arg Met Pro Cys Ala Glu Asp Tyr Leu Ser
645 650 655

Val Val Leu Asn Gln Leu Cys Val Leu His Glu Lys Thr Pro Val Ser
660 665 670

Asp Arg Val Thr Lys Cys Cys Thr Glu Ser Leu Val Asn Arg Arg Pro
675 680 685

Cys Phe Ser Ala Leu Glu Val Asp Glu Thr Tyr Val Pro Lys Glu Phe
690 695 700

Asn Ala Glu Thr Phe Thr Phe His Ala Asp Ile Cys Thr Leu Ser Glu
705 710 715 720

Lys Glu Arg Gln Ile Lys Lys Gln Thr Ala Leu Val Glu Leu Val Lys
725 730 735

His Lys Pro Lys Ala Thr Lys Glu Gln Leu Lys Ala Val Met Asp Asp
740 745 750

Phe Ala Ala Phe Val Glu Lys Cys Cys Lys Ala Asp Asp Lys Glu Thr

```
        755                      760                      765

Cys Phe Ala Glu Glu Gly Lys Lys Leu Val Ala Ala Ser Gln Ala Ala
    770                     775                     780

Leu Gly Leu
785
```

( 2 ) INFORMATION FOR SEQ ID NO:17:

( i ) SEQUENCE CHARACTERISTICS:
( A ) LENGTH: 756 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 3..752

( x i ) SEQUENCE DESCRIPTION: SEQ ID NO:17:

```
CC TTA GGC TTA CAG GTG CAG CTC GAG CAG TCT GGA CCT GAG CTG GTG      47
   Leu Gly Leu Gln Val Gln Leu Glu Gln Ser Gly Pro Glu Leu Val
     1               5                  10                  15

AAG CCT GGG GCC TCA GTG AAG ATT TCC TGC AAA GCT TCT GGC TAC GCA      95
Lys Pro Gly Ala Ser Val Lys Ile Ser Cys Lys Ala Ser Gly Tyr Ala
                 20                  25                  30

TTC AGT AGG TCT TGG ATG AAC TGG GTG AAG CAG AGG CCT GGA CAG GGT     143
Phe Ser Arg Ser Trp Met Asn Trp Val Lys Gln Arg Pro Gly Gln Gly
             35                  40                  45

CTT GAG TGG ATT GGA CGG ATT TAT CCT GGA GAT GGA GAT ACC AAA TAC     191
Leu Glu Trp Ile Gly Arg Ile Tyr Pro Gly Asp Gly Asp Thr Lys Tyr
         50                  55                  60

AAT GGG AAG TTC AAG GGC AAG GCC ACA CTG ACT GCG GAC AGA TCA TCC     239
Asn Gly Lys Phe Lys Gly Lys Ala Thr Leu Thr Ala Asp Arg Ser Ser
     65                  70                  75

AGC ACA GCC TAC ATG CAG CTC AGC AGC CTG ACC TCT GTG GGC TCT GCG     287
Ser Thr Ala Tyr Met Gln Leu Ser Ser Leu Thr Ser Val Gly Ser Ala
 80                  85                  90                  95

GTC TAT TTC TGT GCA AAA GAG AAC AAT AGG TTC GAC GAG AGG GGT TAC     335
Val Tyr Phe Cys Ala Lys Glu Asn Asn Arg Phe Asp Glu Arg Gly Tyr
                100                 105                 110

TAT GCT ATG GAC TAC TGG GGC CAA GGG ACC ACG GTC ACC GTC TCC TCA     383
Tyr Ala Met Asp Tyr Trp Gly Gln Gly Thr Thr Val Thr Val Ser Ser
            115                 120                 125

GGT GGC GGT GGC TCG GGC GGT GGT GGG TCG GGT GGC GGC GGA TCT AAC     431
Gly Gly Gly Gly Ser Gly Gly Gly Gly Ser Gly Gly Gly Gly Ser Asn
        130                 135                 140

ATT CAG TTG ACC CAG TCT CCA AAT TCC ATG TCC ACA TCA GTA GGA GAC     479
Ile Gln Leu Thr Gln Ser Pro Asn Ser Met Ser Thr Ser Val Gly Asp
    145                 150                 155

AGG GTC AGC ATC ACC TGC AAG GCC AGT CAG GAT GTG GAT ACT TCT GTA     527
Arg Val Ser Ile Thr Cys Lys Ala Ser Gln Asp Val Asp Thr Ser Val
160                 165                 170                 175

GCC TGG TAT CAA CAG AAA CCA GGG CAA TCT CCT AAA CTA CTG ATT TAC     575
Ala Trp Tyr Gln Gln Lys Pro Gly Gln Ser Pro Lys Leu Leu Ile Tyr
                180                 185                 190

TGG GCA TCC ACC CGG CAC ACT GGA GTC CCT GAT CGC TTC ACA GGC AGT     623
Trp Ala Ser Thr Arg His Thr Gly Val Pro Asp Arg Phe Thr Gly Ser
            195                 200                 205

GGA TCT GGG ACA GAT TTC ACT CTC ACC ATT AGC AAT GTG CAG TCT GAA     671
Gly Ser Gly Thr Asp Phe Thr Leu Thr Ile Ser Asn Val Gln Ser Glu
        210                 215                 220
```

-continued

GAC TCG GCA GAT TAT TTC TGT CAG CAA TAT AGC AGC TAT CCG TGG ACG 719
Asp Ser Ala Asp Tyr Phe Cys Gln Gln Tyr Ser Ser Tyr Pro Trp Thr
225 230 235

TTC GGT GGA GGG ACC AAG CTG GAG ATC AAA TAAGCTT 756
Phe Gly Gly Gly Thr Lys Leu Glu Ile Lys
240 245 250

( 2 ) INFORMATION FOR SEQ ID NO:18:

( i ) SEQUENCE CHARACTERISTICS:
( A ) LENGTH: 249 amino acids
( B ) TYPE: amino acid
( D ) TOPOLOGY: linear ( i i ) MOLECULE TYPE: protein ( x i ) SEQUENCE DESCRIPTION: SEQ ID NO:18:

Leu Gly Leu Gln Val Gln Leu Glu Gln Ser Gly Pro Glu Leu Val Lys
1 5 10 15

Pro Gly Ala Ser Val Lys Ile Ser Cys Lys Ala Ser Gly Tyr Ala Phe
20 25 30

Ser Arg Ser Trp Met Asn Trp Val Lys Gln Arg Pro Gly Gln Gly Leu
35 40 45

Glu Trp Ile Gly Arg Ile Tyr Pro Gly Asp Gly Asp Thr Lys Tyr Asn
50 55 60

Gly Lys Phe Lys Gly Lys Ala Thr Leu Thr Ala Asp Arg Ser Ser Ser
65 70 75 80

Thr Ala Tyr Met Gln Leu Ser Ser Leu Thr Ser Val Gly Ser Ala Val
85 90 95

Tyr Phe Cys Ala Lys Glu Asn Asn Arg Phe Asp Glu Arg Gly Tyr Tyr
100 105 110

Ala Met Asp Tyr Trp Gly Gln Gly Thr Thr Val Thr Val Ser Ser Gly
115 120 125

Gly Gly Gly Ser Gly Gly Gly Gly Ser Gly Gly Gly Gly Ser Asn Ile
130 135 140

Gln Leu Thr Gln Ser Pro Asn Ser Met Ser Thr Ser Val Gly Asp Arg
145 150 155 160

Val Ser Ile Thr Cys Lys Ala Ser Gln Asp Val Asp Thr Ser Val Ala
165 170 175

Trp Tyr Gln Gln Lys Pro Gly Gln Ser Pro Lys Leu Leu Ile Tyr Trp
180 185 190

Ala Ser Thr Arg His Thr Gly Val Pro Asp Arg Phe Thr Gly Ser Gly
195 200 205

Ser Gly Thr Asp Phe Thr Leu Thr Ile Ser Asn Val Gln Ser Glu Asp
210 215 220

Ser Ala Asp Tyr Phe Cys Gln Gln Tyr Ser Ser Tyr Pro Trp Thr Phe
225 230 235 240

Gly Gly Gly Thr Lys Leu Glu Ile Lys
245

( 2 ) INFORMATION FOR SEQ ID NO:19:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:19:

GGCCNNNNNG GCC 13

( 2 ) INFORMATION FOR SEQ ID NO:20:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid ( i x ) FEATURE:
( A ) NAME/KEY: misc_feature
( B ) LOCATION: 12..14
( D ) OTHER INFORMATION: /note= "NNN is repeated p times"

( x i ) SEQUENCE DESCRIPTION: SEQ ID NO:20:

CCTTAGGCTT ANNNTAAGCT T 21

( 2 ) INFORMATION FOR SEQ ID NO:21:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:21:

GAAATGCATA AGCTCTTGCC ATTCTCACCG 30

( 2 ) INFORMATION FOR SEQ ID NO:22:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:22:

CCCGGGATCC CTTAGGCTTA ACCTGTGAAG CCTGC 35

( 2 ) INFORMATION FOR SEQ ID NO:23:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:23:

CCCGGGATCC AAGCTTAGAC TTGTGCCATG TCG 33

( 2 ) INFORMATION FOR SEQ ID NO:24:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:24:

CCCGGGATCC AAGCTTAGTC CTCCACATAC AG 32

( 2 ) INFORMATION FOR SEQ ID NO:25:

( i ) SEQUENCE CHARACTERISTICS:
( A ) LENGTH: 105 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:25:

CCTTAGGCTT AACCTGTGAA GCCTGCCAGG AGCCGGGAGG CCTGGTGGTG CCTCCCACAG 60

ATGCCCCGGT GAGCCCCACC ACTCTGTATG TGGAGGACTA AGCTT 105

( 2 ) INFORMATION FOR SEQ ID NO:26:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:26:

TTAGGCCTCT GTGACCTTGC CCCTGAAGCC CCTCCTCCTA CTCTGCCCCC CTAAGCTTA 59

( 2 ) INFORMATION FOR SEQ ID NO:27:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:27:

GATCTAAGCT TAGGGGGGCA GAGTAGGAGG AGGGGCTTCA GGGGCAAGGT CACAGAGGCC 60

( 2 ) INFORMATION FOR SEQ ID NO:28:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:28:

CCCGGGATCC CTTAGGCTTA ACCGGTGAAG CCGGC 35

( 2 ) INFORMATION FOR SEQ ID NO:29:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:29:

GGATCCTTAG GGCTGTGCAG CAGGCTACTG GACCTGGTC 39

( 2 ) INFORMATION FOR SEQ ID NO:30:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:30:

GAATTCAAGC TTAACAGAGG TAGCTAACGA TCTCGTCCC 39

( 2 ) INFORMATION FOR SEQ ID NO:31:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:31:

CAAGGATCCA AGCTTCAGGG CTGCGCAAGG TGGCGTAG 38

( 2 ) INFORMATION FOR SEQ ID NO:32:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:32:

CGGGGTACCT TAGGCTTAAC CCCCCTGGGC CCTGCCAGC 39

( 2 ) INFORMATION FOR SEQ ID NO:33:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:33:

TTAGGCTTAG GTGGTGGCGG TACCCCCCTG GGCC 34

( 2 ) INFORMATION FOR SEQ ID NO:34:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:34:

CAGGGGGGTA CCGCCACCAC CTAAGCC 27

( 2 ) INFORMATION FOR SEQ ID NO:35:

( i ) SEQUENCE CHARACTERISTICS:

( A ) LENGTH: 66 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:35:

```
GTTCTACGCC ACCTTGCGCA GCCCGGTGGA GGCGGTGATG CACACAAGAG TGAGGTTGCT     60

CATCGG                                                                66
```

( 2 ) INFORMATION FOR SEQ ID NO:36:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO:36:

```
CAGGGAGCTG GCAGGGCCCA GGGGGGTTCG ACGAAACACA CCCCTGGAAT AAGCCGAGCT     60
```